(12) United States Patent
Fitzgerald et al.

US011391737B2

(10) Patent No.: US 11,391,737 B2
(45) Date of Patent: Jul. 19, 2022

(54) METHODS TO PREDICT PROGRESSION OF BARRETT'S ESOPHAGUS TO HIGH GRADE DYSPLASIA ESOPHAGEAL ADENOCARCINOMA

(71) Applicant: Medical Research Council, Swindon (GB)

(72) Inventors: Rebecca Fitzgerald, Cambridge (GB); Elizabeth Bird-Lieberman, Cambridge (GB)

(73) Assignee: UNITED KINGDOM RESEARCH AND INNOVATION, Swindon (GB)

( * ) Notice: Subject to any disclaimer, the term of this patent is extended or adjusted under 35 U.S.C. 154(b) by 0 days.

(21) Appl. No.: 14/401,725

(22) PCT Filed: May 16, 2013

(86) PCT No.: PCT/GB2013/051254
§ 371 (c)(1),
(2) Date: Nov. 17, 2014

(87) PCT Pub. No.: WO2013/171489
PCT Pub. Date: Nov. 21, 2013

(65) Prior Publication Data
US 2015/0160220 A1    Jun. 11, 2015

(30) Foreign Application Priority Data
May 17, 2012    (GB) .................................. 1208756

(51) Int. Cl.
*C12Q 1/6886* (2018.01)
*G01N 33/574* (2006.01)

(52) U.S. Cl.
CPC ..... *G01N 33/57407* (2013.01); *C12Q 1/6886* (2013.01); *C12Q 2600/158* (2013.01); *G01N 2333/38* (2013.01); *G01N 2333/4739* (2013.01); *G01N 2333/4748* (2013.01); *G01N 2333/70596* (2013.01); *G01N 2400/00* (2013.01); *G01N 2800/06* (2013.01)

(58) Field of Classification Search
None
See application file for complete search history.

(56) References Cited
U.S. PATENT DOCUMENTS

2003/0176646 A1*  9/2003  Newman .......... C07K 14/70503
                                                    530/350
2010/0234762 A1    9/2010  Pond et al.

FOREIGN PATENT DOCUMENTS

WO    2010099543 A2    9/2010

OTHER PUBLICATIONS

Juppner (Bone 1995 vol. 17 No. 2 Supplement 39S-42S).*
Bird-Lieberman et al. (Nature Medicine med 2012 vol. 18 p. 315-321).*
Dolan et al. (Journal of Gastroenterology and Hepatology 2003 vol. 18 p. 683).*
Bird-Lieberman et al (Gut 2011 vol. 60 A169-170 ).*
Conio et al. (Lancet Oncol 2005 vol. 6 p. 311).*
Paulson et al (Clin Cancer Res 2009 vol. 15 p. 3305).*
Matsumura et al. (Journal of Biological chemistry 2007 vol. 282 p. 15700).*
Vial, Manuel et al.; "Epidemiology of Adenocarcinoma of the Esophagus, Gastric Cardia, and Upper Gastric Third"; 2010; Recent Results In Cancer Research; Springer-Verlag, Berlin, Germany, vol. 182; pp. 1-17.
Kadri, Sudarshan et al.; "Acceptability and accuracy of a non-endoscopic screening test for Barrett's oesophagus in primary care: cohort study"; Sep. 10, 2010; British Medical Journal, UK, vol. 341; p. c4372.
Sikkema, Marjolein et al.; "Risk of Esophageal Adenocarcinoma and Mortality in Patients With Barrett's Esophagus: A Systematic Review and Meta-analysis"; Mar. 2010; Clinical Gastroenterology And Hepatology; American Gastroenterological Association, US, vol. 8, Issue 3; pp. 235-244.
Desai, Tusar et al.; "The incidence of oesophageal adenocarcinoma in non-dysplastic Barrett's oesophagus: a meta-analysis"; Jul. 2012; Gut; British Medical Journal, UK, vol. 61, Issue 7; pp. 970-976.
Yousef, Fouad et al.; "The Incidence of Esophageal Cancer and High-Grade Dysplasia in Barrett's Esophagus: A Systematic Review and Meta-Analysis"; Aug. 2008; American Journal of Epidemiology; Johns Hopkins Bloomberg School of Public Health, US, vol. 168, Issue 3; pp. 237-249.
Reid, Brian et al.; "Barrett's oeshopagus and oesophageal adenocarcinoma: time for a new synthesis"; Feb. 2010; National Review Of Cancer; NIH Public Access, US, vol. 10, No. 2; pp. 87-101.

(Continued)

*Primary Examiner* — Katherine D Salmon
(74) *Attorney, Agent, or Firm* — Kenealy Vaidya LLP

(57) ABSTRACT

In some embodiments, a method for aiding prediction of the likelihood of progression from Barrett's esophagus to high grade dysplasia or esophageal adenocarcinoma in a subject, is disclosed. The method can include (a) providing an oesophagal sample from said subject (b) determining if said sample stains abnormally with *Aspergillus oryzae* lectin; (c) determining if there is a DNA content abnormality in said sample; and (d) determining if there is low grade dysplasia in said sample; wherein if (b) is abnormal and (c) is abnormal and low grade dysplasia is present, then an increased likelihood of progression is determined. The disclosed subject matter also relates to an apparatus, and to different uses of certain materials.

10 Claims, 2 Drawing Sheets

Specification includes a Sequence Listing.

(56) References Cited

OTHER PUBLICATIONS

Pepe, Margaret, et al.; "Phases of Biomarker Development for Early Detection of Cancer"; Jul. 18, 2001; Journal Of The National Cancer Institute; National Cancer Institute, US, vol. 93, No. 14; pp. 1054-1061.

Lao-Sirieix, Peter et al.; "Cyclin A Immunocytology as a Risk Stratification Tool for Barrett's Esophagus Surveillance"; Jan. 15, 2007; Clinical Cancer Research; American Association for Cancer Research, US, vol. 13, Issue 2; pp. 659-665.

Reid, Brian et al.; "Predictors of Progression to Cancer in Barrett's Esophagus: Baseline Histologyand Flow Cytometry Identify Low- and High-Risk Patient Subsets"; Jul. 2000; American Journal Of Gastroenterology; Nature Publishing Group, US, vol. 95, Issue 7; pp. 1669-1676.

Rabinovitch, Peter et al.; "Predictors of Progression in Barrett's Esophagus III: Baseline Flow Cytometric Variables"; Nov. 2001; American Journal Of Gastroenterology; Nature Publishing Group, US, vol. 96, Issue 11; pp. 3071-3083.

Dunn, J.M. et al.; "Image cytometry accurately detects DNA ploidy abnormalities and predicts late relapse to high-grade dysplasia and adenocarcinoma in Barrett's oesophagus following photodynamic therapy"; May 25, 2010; British Journal Of Cancer; Cancer Research UK, UK, vol. 102, Issue 11; pp. 1608-1617.

Chao, Dennis et al.; "Cell proliferation, cell cycle abnormalities, and cancer outcome in patients with Barrett's esophagus: A long-term prospective study"; Nov. 1, 2008; Clinical Cancer Research; American Association for Cancer Research, US, vol. 14, Issue 21; pp. 6988-6995.

Casson, A.G. et al.; "p53 alterations in oesophageal cancer: association with clinicopathological features, risk factors, and survival"; Apr. 1998; Journal Of Clinical Pathology: Molecular Pathology; British Medical Journal, UK, vol. 51, No. 2; pp. 71-79.

Ribero Jr., Ulysses et al.; "p53 Sequence Analysis Predicts Treatment Response and Outcome of Patients with Esophageal Carcinoma"; Cancer; Jul. 1, 1998; American Cancer Society, US, vol. 83, No. 1; pp. 7-18.

Kuroki, T. et al.; "Evidence for the presence of two tumour-suppressor genes for hepatocellular carcinoma on chromosome 13q"; Sep. 1995, British Journal Of Cancer; Cancer Research UK, UK, vol. 72, Issue 2; pp. 383-385.

Jorgensen, Trond et al.; "Up-Regulation of the Oligosaccharide Sialyl Lewis X: A New Prognostic Parameter in Metastatic Prostate Cancer"; May 1, 1995; Cancer Research; American Association for Cancer Research, US, vol. 55, Issue 9; pp. 1817-1819.

Futamura, N. et al.; "Clinicopathologic significance of sialyl LeX expression in advanced gastric carcinoma"; Dec. 2000; British Journal Of Cancer, Cancer Research UK, UK, vol. 83, Issue 12; 1681-1687.

Bird-Lieberman, Elizabeth et al.; "Molecular imaging using fluorescent lectins permits rapid endoscopic identification of dysplasia in Barrett's esophagus"; Jan. 2012; Nature Medicine; Nature Publishing Group, US, vol. 18, No. 2; pp. 315-322.

Murray, Liam et al.; "Risk of adenocarcinoma in Barrett's oesophagus: population based study"; Sep. 6, 2003; British Medical Journal; British Medical Journal, UK, vol. 327; pp. 534-535.

Coleman, Helen et al.; "Increasing incidence of Barrett's oesophagus: a population-based study"; 2011; European Journal Of Epidemiology; Springer, Berlin, Germany, vol. 26, Issue 9; pp. 739-745.

Bhat, Shivaram et al.; "Risk of Malignant Progression in Barrett's Esophagus Patients: Results from a Large Population-Based Study"; Aug. 13, 2011; Journal Of The National Cancer Institute; National Cancer Institute, US, vol. 103, Issue 13; pp. 1-9.

Schlemper, R. J. et al.; "The Vienna classification of gastrointestinal epithelial neoplasia"; Aug. 2000; Gut; British Medical Journal, UK, vol. 47, Issue 2; pp. 251-255.

Pretorius, Maria et al.; "Large scale genomic instability as an additive prognostic marker in early prostate cancer"; Jul. 24, 2009; Cellular Oncology; Springer, Berlin, Germany, vol. 31 No. 4; pp. 251-259.

Bondi, Johan et al.; "Large-scale genomic instability in colon adenocarcinomas and correlation with patient outcome"; 2009; APMIS; Wiley Online Library, US, vol. 117, Issue 10; pp. 730-736.

Haroske, G. et al.; "Fourth updated ESACP consensus report on diagnostic image cytometry"; Analytical Cellular Pathology; Jan. 1, 2001; IOS Press, Amsterdam, Netherlands, vol. 23, Issue 2; pp. 89-95.

Cronin, James et al.; "Epidermal Growth Factor Receptor (EGFR) Is Overexpressed in High-Grade Dysplasia and Adenocarcinoma of the Esophagus and May Represent a Biomarker of Histological Progression in Barrett's Esophagus (BE)"; Jan. 2011; American Journal Of Gastroenterology; Nature Publishing Group, US, vol. 106, Issue 1; pp. 46-56.

Baker, Stuart et al.; "Markers for early detection of cancer: Statistical guidelines for nested case-control studies"; Feb. 28, 2002; BMC Medical Research Methodology; BioMed Central, London, UK, vol. 2, Issue 4; pp. 1-8.

Pencina, Michael et al.; "Evaluating the added predictive ability of a new marker: From area under the ROC curve to reclassification and beyond"; Jan. 30, 2008; Statistics In Medicine; Wiley InterScience, US, vol. 27, Issue 2; pp. 157-172.

Steyerberg, Ewout et al.; "Internal validation of predictive models: Efficiency of some procedures for logistic regression analysis"; Aug. 2001; Journal Of Clinical Epidemiology; Elsevier, US, vol. 54, Issue 8; pp. 774-781.

Galipeau, Patricia et al.; "NSAIDs Modulate CDKN2A, TP53, and DNA Content Risk for Progression to Esophageal Adenocarcinoma"; Feb. 27, 2007; PLOS Medicine; PLoS, US, vol. 4, Issue 2; pp. 342-354.

Schulmann, Karsten et al.; "Inactivation of p16, RUNX3, and HPP1 occurs early in Barrett's-associated neoplastic progression and predicts progression risk"; Jun. 2005, Oncogene, Nature Publishing Group, US, vol. 24, Issue 25; pp. 4138-4148.

Reid, Brian et al.; "Predictors of Progression in Barrett's Esophagus II: Baseline 17p (p53) Loss of Heterozygosity identifies a Patient Subset at Increased Risk for Neoplastic Progression"; Oct. 2001; American Journal Of Gastroenterology; Nature Publishing Group, US, vol. 96, Issue 10; pp. 2839-2848.

Reid, Brian et al.; "Flow-Cytometric and Histological Progression to Malignancy in Barrett's Esophagus: Prospective Endoscopic Surveillance of a Cohort"; Apr. 1992; Gastroenterology; American Gastroenterological Association, US, vol. 102, No. 4; pp. 1212-1219.

Paulson, Thomas et al.; "Chromosomal instability and copy number alterations in Barrett's esophagus and esophageal adenocarcinoma"; May 15, 2009; Clinical Cancer Research; American Association for Cancer Research, US, vol. 15, No. 10; pp. 3305-3314.

Bird-Lieberman, Elizabeth et al.; "Phase 2 and Phase 3 Multicentre Studies Demonstrate the Potential for Glycans as Predictive Biomarkers in Barrett's Oesophagus"; Apr. 2011; Gut; British Medical Journal, UK, vol. 60, Supplement 1; pages A169-A170.

Hvid-Jensen, Frederik et al.; "Incidence of Adenocarcinoma among Patients with Barrett's Esophagus"; Oct. 13, 2011; The New England Journal Of Medicine; Massachusetts Medical Society, US, vol. 365, No. 15; pp. 1375-1383.

Wani, Sachin et al.; "Risk Factors for Progression of Low-Grade Dysplasia in Patients With Barrett's Esophagus"; Oct. 2011; Gastroenterology; American Gastroenterological Association, US, vol. 141, No. 4; pp. 1179-1186.

Bulsiewicz, William et al.; "The Role of Radiofrequency Ablation in the Management of Barrett's Esophagus"; 2011; Gastrointestinal Endoscopy Clinics Of North America; Gastrointestinal Endoscopy Clinics of North America, US, vol. 21, Issue 1; pp. 95-110.

Spechler, Stuart et al.; "American Gastroenterological Association Medical Position Statement on the Management of Barrett's Esophagus"; Mar. 2011; Gastroenterology; American Gastroenterological Association, US, vol. 140, No. 3; pp. 1084-1091.

Sikkema, Marjolein et al.; "Risk of Esophageal Adenocarcinoma and Mortality in Patients With Barrett's Esophagus: A Systematic Review and Meta-Analysis"; 2010; Clinical Gastroenterology And Hepatology; American Gastroenterological Association, US, vol. 8, No. 3; pp. 235-244.

(56) References Cited

OTHER PUBLICATIONS

Alsner, Jan et al.; "A comparison between p53 accumulation determined by immunohistochemistry and TP53 mutations as prognostic variables in tumours from breast cancer patients"; 2008; Acta Oncologica; Taylor & Francis Online, UK, vol. 47, Issue 4; pp. 600-607.

* cited by examiner

METHODS TO PREDICT PROGRESSION OF BARRETT'S ESOPHAGUS TO HIGH GRADE DYSPLASIA ESOPHAGEAL ADENOCARCINOMA

CROSS REFERENCE TO RELATED APPLICATIONS

This application is a national phase filing under 35 C.F.R. § 371 of and claims priority to PCT Patent Application No. PCT/GB2013/051254, filed on May 16, 2013, which claims the priority benefit under 35 U.S.C. § 119 of British Patent Application No. 1208756.5, filed on May 17, 2012, which are hereby incorporated in their entireties by reference.

SEQUENCE LISTING

The instant application contains a Sequence Listing which has been submitted electronically in ASCII format and is hereby incorporated by reference in its entirety. Said ASCII copy, created on Jan. 10, 2017, is named 5053-0004_SL.txt and is 11,885 bytes in size.

FIELD OF THE INVENTION

The invention relates to the prediction of progression from Barrett's Esophagus to high grade dysplasia or esophageal adenocarcinoma. In particular the invention relates to methods for aiding the prediction of likelihood of this progression.

BACKGROUND TO THE INVENTION

Gastroesophageal reflux can lead to Barrett's oesophagus (BE), in which the squamous epithelium of the distal oesophagus is replaced by columnar epithelium. BE is found in 3% of patients undergoing endoscopy for reflux symptoms and 1% of all those undergoing endoscopy (1, 2). The importance of BE lies in its potential to progress, via a metaplasia-dysplasia-adenocarcinoma sequence, to esophageal adenocarcinoma (EAC). EAC continues to carry a dismal prognosis with an overall five year survival rate of less than 20% (3).

The rate of progression from non-dysplastic BE (NDBE) to EAC is in the region of 0.2-0.5% per year based on recent meta-analyses (4-6), and large population-based studies. This represents a small but significantly increased relative risk over the general population. Counselling individual patients is difficult as the majority of patients with NDBE will not progress to EAC and our ability to predict who is at risk is, at present, severely limited (4). This is a problem in the art.

Endoscopic surveillance programmes, to monitor for progression from NDBE to dysplasia or EAC, are very costly and require highly skilled endoscopists. In addition, they have questionable cost effectiveness and their value in reducing cancer mortality is unproven.

There is a growing body of evidence that the majority of EACs arising in BE occur in association with chromosomal instability, characterised by widespread imbalances in chromosome number (aneuploidy/tetraploidy) and loss of heterozygosity. These karyotypic abnormalities are often associated with the accumulation of mutations in specific tumour suppressor genes and oncogenes associated with cancer initiation and progression (7). The Early Detection Research Network (EDRN) has defined a pathway through which putative biomarkers must be validated prior to being applicable to routine clinical use (8). Several biomarkers which have potential for clinical use in BE have been identified in cross-sectional Phase 2 and 3 studies. Surface expression of cyclin A, a marker of a proportion of proliferating cells, has previously been shown to correlate with the degree of dysplasia within BE, and can be assessed using histochemistry (9). DNA content abnormalities (aneuploidy/tetraploidy) previously measured by flow cytometry (10, 11) can also be accurately assessed using image cytometry DNA analysis (DNA copy number), which can be applied to paraffin sections (12). Inactivation of the tumour-suppressor p53 gene has been identified as a key event in the development of EAC and bi-allelic inactivation of p53 has been associated with subsequent development of EAC (13).

Coordinated changes in glycan expression have been shown to occur in the development of EAC. Gene expression analysis indicated that the majority of genes which contributed most to enrichment of glycan pathways in the progression to EAC had a role in the synthesis of Lewis antigens, which are known to alter in other cancers (16-18). A Phase 3 study (using immunohistochemistry) of Lewis antigens confirmed that sLeo (also known as CA19-9) and $Le^x$ (CD15) expression was associated with the degree of dysplasia within BE. The lectins (specific glycan-binding proteins) Wheat germ agglutinin (WGA) and *Aspergillus oryzae* lectin (AOL) have also been shown by lectin histochemistry to have highly significant decreased binding in the progression to EAC (19).

Objective markers individualising the risk of progression at BE diagnosis would allow clinicians to target interventions such as endoscopic surveillance or minimally invasive therapy to those at high risk, whereas those at low risk could be reassured and avoid unnecessary and costly follow up. However, no such individualised risk assessment is currently possible, and no reliable molecular predictors of progression from BE to EAC are known, which are problems in the art.

The present invention seeks to overcome problem(s) associated with the prior art.

SUMMARY OF THE INVENTION

The risk of progression to esophageal adenocarcinoma (EAC) from Barrett's Esophagus (BE) is low and unpredictable. Accurate risk prediction tools are absent from the prior art.

The inventors considered a wide range of candidate markers including $sLe^a$, $Le^x$, sialic acid residues detected by WGA and the Fucα1-6GlcNAc residues detected by AOL to predict progression to EAC in BE. In addition, early molecular changes, seen even prior to the advent of dysplasia, were considered as possible biomarkers of the risk of progression to EAC. However there was no teaching in the art that any such markers had any predictive value for the key parameter of progression to EAC. The inventors tackled these problems by designing a study to assess the performance of candidate biomarkers in predicting neoplastic progression in BE and to create a biomarker panel as a risk stratification tool.

We disclose a phase 3 population-based study which reveals new risk-stratification biomarker panels for Barrett's esophagus. As a result of this study, the inventors have been able to derive small and focused panels of biomarkers which provide a statistically robust prediction tool for progression to EAC. This new ability to predict progression to EAC is itself a significant advance. Moreover, use of this tool enables further benefits such as the optimisation of surveillance and intervention regimes.

DETAILED DESCRIPTION OF THE INVENTION

In one aspect, the invention relates to a method for aiding prediction of the likelihood of progression from Barrett's esophagus to high grade dysplasia or esophageal adenocarcinoma in a subject, the method comprising (a) providing an oesophagal sample from said subject (b) determining if said sample stains abnormally with *Aspergillus oryzae* lectin;

(c) determining if there is a DNA content abnormality in said sample; and (d) determining if there is low grade dysplasia in said sample;

wherein if (b) is abnormal and (c) is abnormal and low grade dysplasia is present, then an increased likelihood of progression is determined.

*Aspergillus oryzae* lectin suitably corresponds to the sequence of EMBL accession number BAB88318 such as

```
                                           (SEQ ID NO: 1)
MSTPGAQEVLFRTGIAAVNSTNHLRVYFQDSHGSIRESLYESGWANGTA

KNVIAKAKLGTPLAATSKELKNIRVYSLTEDNVLQEAAYDSGSGWYNGA

LAGAKFTVAPYSRIGSVFLAGTNALQLRIYAQKTDNTIQEYMWNGDGWK

EGTNLGVALPGTGIGVTCWRYTDYDGPSIRVWFQTDNLKLVQRAYDPHT

GWFKELTTIFDKAPPRCAIAATNFNPGKSSIYMRIYFVNSDNTIWQVCW

DHGQGYHDKRTITPVIQGSEIAIISWEGPELRLYFQNGTYVSAISEWSW

ARHGSQLGRRALPPAE
```

An increased likelihood of progression means a likelihood of progression which is higher than the standard or normal risk of progression for an equivalent subject which does not show the specified abnormal markers. In other words, the subject with a higher likelihood of progression has a greater chance of progressing to EAC.

An equivalent subject is suitably matched for as many as possible of the basic criteria such as age, sex, etc. Choice of control subjects is well known in clinical research, and is discussed in more detail below and in the examples section.

In another aspect, the invention relates to a method as described above further comprising the step of (e) determining if said sample stains abnormally for CA19-9;

wherein if (b) is abnormal and (c) is abnormal and low grade dysplasia is present, and if (e) is abnormal then a further increased likelihood of progression is determined.

CA19-9 is also known as Lewis antigen sLe$^a$ and is well known in the art; in case any further guidance is needed reference is made to CAS-No. 92448-22-1.

In another aspect, the invention relates to a method as described above further comprising the step of (f) determining if said sample stains abnormally for Cyclin A;

wherein if (b) is abnormal and (c) is abnormal and low grade dysplasia is present, and if (f) is abnormal then a further increased likelihood of progression is determined.

Cyclin A suitably means NCBI accession number CAA02087. Suitably this has a sequence of

```
                                                                      (SEQ ID NO: 2)
  1 mlgnsapgpa trealgaasi aadgaprgpg eyqpgkgsar pttadpgala vlksgnprgl 61 aheqrpktrr vaplkdlpvn dehvtvppwk anskqpafti hvdeaekeaq kkpaesqkie 121 redalafnsa islpgprkpl vpldypmdgs fesphtmdms ivledekpvs vnevpdyhed 181 ihtylremev kckpkvgymk kqpditnsmr ailvdwlvev geeyklqnet lhlavnyidr 241 flssmsvlrg klqlvgtaam llaskfeeiy ppevaefvyi tddtytkkqv lrmehlvlkv 301 ltfdlaaptv nqfltqyflh qqpanckves lamflgelsl idadpylkyl psviagaafh 361 lalytvtgqs wpeslirktg ytleslkpcl mdlhqtylka pqhaqqsire kyknskyhgv 421 sllnppetln l
```

In another aspect, the invention relates to a method as described above further comprising the step of (g) determining if said sample stains abnormally for p53;

wherein if (b) is abnormal and (c) is abnormal and low grade dysplasia is present, and if (g) is abnormal then a further increased likelihood of progression is determined.

p53 suitably means NCBI accession number AAD28535. Suitably this has a sequence of:

```
                                                                      (SEQ ID NO: 3)
  1 meepqsdpsv epplsqeffs dlwkllpenn vlsplpsqam ddlmlspddi eqwftedpgp 61 deaprmpeaa prvapapaap tpaapapaps wplsssvpsq ktyqgsygfr lgflhsgtak 121 svtctyspal nkmfcqlakt cpyqlwvdst pppgtrvram aiykqsqhmt evvrrcphhe
```

```
-continued
181 rcsdsdglap pqhlirvegn lrveylddrn tfrhsvvvpy eppevgsdct tihynymcns 241 scmggmnrrp iltiitleds sgnllgrnsf evrvcacpgr drrtekenlr kkgephhelp 301 pgstkralpn ntssspqpkk kpldgeyftl qirgrerfem frelnealel kdaqagkepg 361 gsrahsshlk skkgqstsrh kklmfktegp dsd
```

In another aspect, the invention relates to a method as described above further comprising the step of (h) determining if said sample stains abnormally with Wheat Germ Agglutinin lectin; wherein if (b) is abnormal and (c) is abnormal and low grade dysplasia is present, and if (h) is abnormal then a further increased likelihood of progression is determined.

Wheat Germ Agglutinin lectin suitably means NCBI accession number AAA34257.1 or GI: 170668. Suitably this has sequence of

```
                                                      (SEQ ID NO: 4)
  1 qrcgeqgsgm ecpnnlccsq ygycgmggdy cgkgcqngac wtskrcgsqa ggktcpnnhc 61 csqyghcgfg aeycgagcqg gpcradikcg sqaggklcpn nlccsqwgyc glgsefcgeg 121 cqngacstdk pcgkdaggrv ctnnyccskw gscgigpgyc gagcqsggcd gvfaeaiatn 181 stllae
```

In another aspect, the invention relates to a method as described above further comprising the steps of (f) determining if said sample stains abnormally for Cyclin A;

(g) determining if said sample stains abnormally for p53;

(h) determining if said sample stains abnormally with Wheat Germ Agglutinin lectin; wherein if (b) is abnormal and (c) is abnormal and low grade dysplasia is present, and if (f) is abnormal and (g) is abnormal and (h) is abnormal then a further increased likelihood of progression is determined.

In another aspect, the invention relates to a method as described above further comprising the steps of (f) determining if said sample stains abnormally for Cyclin A;

(g) determining if said sample stains abnormally for p53;

(h) determining if said sample stains abnormally with Wheat Germ Agglutinin lectin; wherein if (b) is abnormal and (c) is abnormal and low grade dysplasia is present, and if (e) is abnormal and (f) is abnormal and (g) is abnormal and (h) is abnormal then a further increased likelihood of progression is determined.

In another aspect, the invention relates to an assay for selecting a treatment regimen, said assay comprising (a) providing an oesophagal sample from said subject (b) determining if said sample stains abnormally with *Aspergillus oryzae* lectin;

(c) determining if there is a DNA content abnormality in said sample; and (d) determining if there is low grade dysplasia in said sample;

wherein if (b) is abnormal and (c) is abnormal and low grade dysplasia is present, then a treatment regimen of increased surveillance is selected.

Increased surveillance may mean that additional surveillance techniques are applied to the subject, or may mean that additional surveillance events are applied to the subject.

Suitably increased surveillance means that additional surveillance events are applied to the subject. In other words, suitably increased surveillance means that the subject is monitored more frequently (i.e. more often) if a treatment regimen of increased surveillance is selected. 'Increased' means a higher (more frequent) rate of surveillance events than the subject was receiving before the assay was carried out. In other words, suitably increased surveillance means a reduction in the interval between surveillance events for that subject. Clearly individual subjects may be under individual surveillance regimens based on their clinical history. Thus, 'increased' surveillance or reduction of the interval between surveillance events must be judged on a subject-by-subject basis rather than an absolute value for (e.g.) surveillance intervals. This is explained in more detail in example 2.

Surveillance is not regarded as a method of treatment of the human or animal body, but is rather regarded as having its natural meaning of monitoring. Thus suitably if the regimen selected relates only to surveillance, then suitably the assay is for selecting a surveillance regimen and may not involve treatment of the human or animal body.

In another aspect, the invention relates to an apparatus or a system which is (a) configured to analyse an oesophagal sample from a subject, wherein said analysis comprises (b) determining if said sample stains abnormally with *Aspergillus oryzae* lectin;

(c) determining if there is a DNA content abnormality in said sample; and (d) determining if there is low grade dysplasia in said sample;

said apparatus or system comprising an output module, wherein if (b) is abnormal and (c) is abnormal and low grade dysplasia is present, then said output module indicates an increased likelihood of progression to EAC for said subject.

Suitably the sample comprises formalin fixed paraffin embedded material.

*Aspergillus oryzae* lectin

Suitably *Aspergillus oryzae* lectin staining may be determined by any suitable method known in the art. Suitably it is determined by a method suitable for use on FFPE material.

More suitably step (b) comprises determining the level of staining by *Aspergillus oryzae* lectin in said sample by grading the intensity of the stain and the percentage of the area stained at said intensity, and producing an H score for said stain.

DNA Content Abnormality

Suitably determining whether there is a DNA content abnormality may be done by any suitable method known in the art. Suitably it is determined by a method suitable for use on FFPE material.

More suitably step (c) comprises determining the DNA content by image cytometry DNA analysis and inferring from said determination whether said DNA content is abnormal. Using this detection technique has the advantage of overcoming many of the technical difficulties associated with flow cytometric detection, which is the standard in the art.

Low Grade Dysplasia

Suitably determining whether there is low grade dysplasia may be done by any suitable method known in the art. Suitably it is determined by a method suitable for use on FFPE material.

More suitably step (d) comprises histological examination of the sample, and scoring the presence or absence of low grade dysplasia using the Vienna scale.

The Vienna scale is a well-known standard for scoring dysplasia, and is described in detail in the art such as in Schlemper R J, Riddell R H, Kato Y, et al. The Vienna classification of gastrointestinal epithelial neoplasia. Gut. 2000 Aug. 1, 2000; 47(2):251-5, which is incorporated herein by reference specifically for the technique of scoring lesions according to the Vienna scale.

CA19-9 (Lewis Antigen sLe$^a$)

Suitably determining whether there is abnormal staining for CA19-9 may be done by any suitable method known in the art. Suitably it is determined by a method suitable for use on FFPE material.

More suitably step (e) comprises immunohistochemical staining of the sample for CA19-9, grading the intensity of the stain and the percentage of the area stained at said intensity, and producing an H score for said stain.

Cyclin A

Suitably determining whether there is abnormal staining for Cyclin A may be done by any suitable method known in the art. Suitably it is determined by a method suitable for use on FFPE material.

More suitably step (f) comprises immunohistochemical staining of the sample for Cyclin A, determining the percentage of Cyclin A positive epithelial surface cells compared to Cyclin A negative epithelial surface cells, wherein a percentage of 1% or more Cyclin A positive epithelial surface cells is an abnormal stain.

p53

Suitably determining whether there is abnormal staining for p53 may be done by any suitable method known in the art. Suitably it is determined by a method suitable for use on FFPE material.

More suitably step (g) comprises immunohistochemical staining of the sample for p53, and scoring the stain as normal or abnormal wherein either a strong, dark stain compared to background stain or an absence of stain compared to background stain is an abnormal stain.

Wheat Germ Agglutinin Lectin

Suitably Wheat Germ Agglutinin lectin staining may be determined by any suitable method known in the art. Suitably it is determined by a method suitable for use on FFPE material.

More suitably step (h) comprises determining the level of staining by Wheat Germ Agglutinin lectin in said sample by grading the intensity of the stain and the percentage of the area stained at said intensity, and producing an H score for said stain.

In another aspect, the invention relates to use for prognostic or risk prediction applications relating to high grade dysplasia or esophageal adenocarcinoma, of a material which recognises, binds to or has affinity for a polypeptide selected from p53, Cyclin A, or CA19-9, or a fragment, variant or mutant thereof. In another aspect, the invention relates to use of a combination of materials, each of which respectively recognises, binds to or has affinity for one or more of said polypeptide(s), or a fragment, variant or mutant thereof. Suitably said material comprises an antibody or fragment thereof such as an antigen binding fragment thereof.

Antibodies may be polyclonal or monoclonal, and may be multispecific (including bispecific), chimeric or humanised antibodies. Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Examples of antibody fragments, capable of binding an antigen or other binding partner, are the Fab fragment consisting of the VL, VH, CI and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Antibody fragments, which recognise specific epitopes, may be generated by known techniques. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternative, Fab expression libraries may be constructed (Huse, et al., 1989, Science 246: 1275-1281) to allow rapid and easy identification of monoclonal Fab fragments with the desired specificity.

In another aspect, the invention relates to use for prognostic or risk prediction applications relating to high grade dysplasia or esophageal adenocarcinoma, of *Aspergillus oryzae* lectin or Wheat Germ Agglutinin lectin.

In another aspect, the invention relates to use for prognostic or risk prediction applications relating to high grade dysplasia or esophageal adenocarcinoma, of image cytometry DNA analysis.

In another aspect, the invention relates to an assay device comprising a material which binds to or has affinity for a polypeptide selected from p53, Cyclin A, or CA19-9 and which further comprises *Aspergillus oryzae* lectin and/or Wheat Germ Agglutinin lectin.

Suitably said lectin comprises a detectable label.

In all cases, if (b) is normal and/or (c) is normal and/or low grade dysplasia is absent, then there is no determination of increased likelihood of progression to EAC. In these embodiments, no increased surveillance would be indicated and no minimally invasive therapy would be indicated.

In all cases, CD15 does not have predictive value. CD15 is suitably not assayed in the present invention. Data relating to CD15 are included for comparison purposes to demonstrate the benefits which the predictive markers of the invention provide.

The invention may be used in connection with high grade dysplasia or esophageal adenocarcinoma. Suitably the invention is in connection with high grade dysplasia. This has the advantage of allowing earlier intervention. More suitably the invention is in connection with esophageal adenocarcinoma. This has the advantage of treating a more threatening condition.

Definitions

The term 'comprises' (comprise, comprising) should be understood to have its normal meaning in the art, i.e. that the stated feature or group of features is included, but that the term does not exclude any other stated feature or group of features from also being present.

Abnormal Vs Normal

It is believed that the skilled reader can determine whether or not the markers are normal or abnormal using the guidance given above. However, in case further explanation is helpful, this categorisation may be carried out as follows:

Each biomarker score is dichotomised into abnormal or normal.

For DNA copy number, p53 and cyclin A this is on the basis of a priori knowledge (for example for DNA copy number diploid is normal, tetraploidy or aneuploidy is abnormal).

For CA 19-9, WGA, AOL and CD-15, each of the components of the staining score (most suitably each of four components as described below) were dichotomised into normal/abnormal based on the most frequent median distribution amongst controls and then summed to give an overall abnormal score of 0-4 for each biomarker.

The term 'mutant' of a biomarker such as a polypeptide biomarker of the invention should have its normal meaning in the art. Mutants are sometimes referred to as 'variants' or 'alleles'. The key is to detect biomarkers as have been set out herein. The biomarkers may possess individual variations in the form of mutations or allelic variants between individuals being studied. Therefore there may be some degree of deviation from the exemplary SEQ ID NOs provided herein. The SEQ ID NOs provided herein are to assist the skilled reader in identifying and working with the polypeptides/biomarkers of the invention and are not intended as a restricted and inflexible definition of the individual polypeptides being assayed. Thus minor sequence differences between the SEQ ID NOs provided and the actual sequences of the polypeptide biomarkers being detected will be expected within the boundaries of normal variation between subjects. This should not affect the working of the invention.

Fragments/Peptides

It will be appreciated by the skilled worker that the details of the biomarkers discussed herein and in particular the sequences presented for them are given to facilitate their detection. The important information being gathered is the presence or absence (or particular level) of the biomarker in the sample being studied. There is no particular requirement that the full length polypeptide be scored. Therefore the invention embraces the detection of fragments of the polypeptide/lectin biomarkers. Moreover, the kits and peptides of the invention may comprise fragments of the polypeptides and need not comprise the full length sequences exemplified herein.

Thus a fragment is suitably at least 6 amino acids in length, suitably at least 7 amino acids in length, suitably at least 8 amino acids in length, suitably at least 9 amino acids in length, suitably at least 10 amino acids in length, suitably at least 15 amino acids, suitably at least 25 amino acids, suitably at least 50 amino acids, suitably at least 100 amino acids, or suitably the majority of the biomarker polypeptide of interest.

Sample

The sample may be from a subject. The subject is suitably a mammal, most suitably a human.

Suitably the methods do not involve actual collection of the sample. Suitably the sample is an in vitro sample.

Methods of the invention are suitably performed on an isolated sample from the subject being investigated. Thus, suitably the methods are methods which may be conducted in a laboratory setting without the need for the subject to be present. Suitably the methods are carried out in vitro i.e. suitably the methods are in vitro methods.

Suitably the sample is from a subject having Barrett's Esophagus.

Suitably the sample comprises material taken from the region of the Barrett's Esophagus.

Suitably the sample comprises material taken from the Barrett's Esophagus segment itself.

Suitably the sample is a biopsy.

Suitably the sample comprises formalin fixed paraffin embedded (FFPE) material. It is an advantage of the invention that the methods can be carried out on FFPE material.

Clinically obtained samples are often processed into FFPE material. Therefore the invention may be practiced very widely.

Suitably each of the markers described herein may be detected in FFPE material. Although there are a range of techniques for assaying the markers described, most suitably those techniques which can be carried out on FFPE material are used. This provides the advantage that only one sample is needed in order to assess multiple markers as described herein.

Reference Standard

The reference standard typically refers to a sample from a healthy individual i.e. one who does not have EAC. The reference standard may be from a healthy individual who has BE but does not have HGD/EAC, most suitably does not have EAC.

Moreover, controls may be chosen with greater precision depending on which marker is being considered. For example if considering AOL then it may be advantageous to choose a control of BE without dysplasia or EAC. For example if ploidy is being considered then it may be advantageous to choose a control of any normal tissue (normal squamous oesophagus for example).

The reference standard can an actual sample analysed in parallel. Alternatively the reference standard can be one or more values previously derived from a comparative sample e.g. a sample from a healthy subject. In such embodiments a mere numeric comparison may be made by comparing the value determined for the sample from the subject to the numeric value of a previously analysed reference sample. The advantage of this is not having to duplicate the analysis by determining concentrations in individual reference samples in parallel each time a sample from a subject is analysed.

Suitably the reference standard is matched to the subject being analysed e.g. by gender e.g. by age e.g. by ethnic background or other such criteria which are well known in the art. The reference standard may be a number such as an absolute concentration drawn up by one or more previous studies.

Reference standards may suitably be matched to specific patient sub-groups e.g. elderly subjects, or those with a previous relevant history such as acid reflux or BE.

Suitably the reference standard is matched to the sample type being analysed. For example the concentration of the biomarker polypeptide(s) being assayed may vary depending on the type or nature of the sample. It will be immediately apparent to the skilled worker that the concentration value(s) for the reference standard should be for the same or a comparable sample to that being tested in the method(s) of the invention. For example, if the sample being assayed is from the Barrett's segment then the reference standard value should be for Barrett's segment to ensure that it is capable of meaningful cross-comparison. Suitably the sample type for the reference standard and the sample type for the subject of interest are the same.

Where H scores are determined for staining of the sample, determination of whether the stain is normal or abnormal is suitably carried out by comparing the determined H score to a reference standard H score (such as the most frequent median distribution amongst sample(s) from control subjects) and inferring from said comparison whether said staining is abnormal.

Risk Scoring

It is possible to quantify the risk for an individual subject depending on their particular scores for the various markers in the panels of the invention.

Risk of Progression—Individual Biomarkers

Table 2 illustrates the risk of progression from BE to HGD/cancer for each of the individual biomarkers. Dysplasia in BE patients who progressed (cases) was more frequently diagnosed in the clinical setting, compared with dysplasia scored by two blinded expert gastrointestinal pathologists, although the latter score had superior specificity. Dysplasia, DNA copy number, CA 19-9 and AOL abnormalities were all significantly directly associated with risk of progression, while cyclin A, p53 and WGA abnormalities showed non-significant tendencies towards an increased risk of progression. CD-15 abnormalities were not associated with progression risk in this patient group. It should be noted, however, that sensitivity and specificity of the individual biomarkers were low as reflected in the true and false prediction rates (TPR and FPR). Analysis restricted to cancer outcomes alone resulted in largely similar results to the combined analysis for HGD and EAC, with the exception of p53 which became significantly associated with an increased risk of progression from BE to cancer (OR 1.95; 95% CI: 1.04-3.67).

Combination Seven Biomarker Panel Model

Table 3 shows effect estimates from the logistic regression models after combining all seven biomarkers (along with dysplasia and year of BE, age and sex adjusted for by study design) into a risk score and shows estimates of the performance of this risk score. The c statistic from the seven biomarker model was relatively high (c statistic=0.78) and maintained after internal validation using bootstrap sampling techniques (optimism corrected c statistic=0.71).

It is important to note that this seven biomarker model was able to better discriminate cases and controls, compared with a basic clinical model (containing just dysplasia, age, sex and year of BE), reflected by an improvement in the c statistic of 0.15 (FIG. 1). Table 3 also illustrates similar improvements in discrimination slopes (i.e. the difference in mean predicted probability of being a case from the model in the case and controls) for the models containing seven biomarkers (0.22) and from the basic model (0.07). In a similar analysis restricted to non-dysplastic BE individuals (76% cases and 74% controls), the c statistic for the seven biomarker model was lower than that observed for all BE patients (optimism corrected c statistic=0.63) but still represented some improvement over the basic model (optimism corrected c statistic=0.43). Similarly, the IDI of 0.13 indicated that the seven biomarker model improved discriminative ability compared with the basic model.

Reduced Biomarker Panel Model

It was noted that several biomarkers in the full model were not significantly contributing to the overall model. Furthermore, the smaller the biomarker panel the easier it would be to apply this in routine clinical practice. We therefore set out to construct a reduced model by applying a backward selection procedure. Table 4 shows the performance of this reduced model (AOL and DNA copy number) compared with basic model (age, sex and year of BE) and the 7 biomarker model (FIG. 1). It can be seen that this model was equivalent to the seven biomarker model in discriminating cases and controls. It should however be noted that there are large confidence intervals for this analysis in view of the small number of patients.

A risk score was then created for individuals who may be abnormal for one, two or all of these markers, as shown in Table 5. For each 1 point increase in risk score, dysplastic BE patients are almost at four-fold increased risk of progressing to develop EAC (OR 3.75; 95% CI: 2.42-5.79), while NDBE patients have a three-fold increased progression risk (OR 2.99; 95% CI: 1.72-5.20).

Thus in some embodiments the invention relates to a method as described herein, further comprising the step of determining a risk score for the subject. Suitably the risk score is determined from the individual marker/panel results as explained herein.

Suitably the method may further comprise ascribing a risk of progressing to develop EAC. Suitably this risk is derived using the risk score determined from the individual marker/panel results as above.

Further Embodiments

In another aspect, the invention relates to an assay for selecting a treatment regimen, said assay comprising (a) providing an oesophagal sample from said subject (b) determining if said sample stains abnormally with *Aspergillus oryzae* lectin;

(c) determining if there is a DNA content abnormality in said sample; and (d) determining if there is low grade dysplasia in said sample;

wherein if (b) is abnormal and (c) is abnormal and low grade dysplasia is present, then a treatment regimen of increased surveillance is selected.

Suitably said assay further comprises the step of (e) determining if said sample stains abnormally for CA 19-9;

wherein if (b) is abnormal and (c) is abnormal and low grade dysplasia is present, and if (e) is abnormal then a treatment regimen of increased surveillance is selected. More suitably a treatment regimen of minimally invasive therapy may be recommended.

Suitably said assay further comprises the step of
(f) determining if said sample stains abnormally for Cyclin A;
wherein if (b) is abnormal and (c) is abnormal and low grade dysplasia is present, and
if (e) is abnormal then a treatment regimen of increased surveillance is selected. More suitably a treatment regimen of minimally invasive therapy may be recommended.

Suitably said assay further comprises the step of
(g) determining if said sample stains abnormally for p53;
wherein if (b) is abnormal and (c) is abnormal and low grade dysplasia is present, and
if (e) is abnormal then a treatment regimen of increased surveillance is selected. More suitably a treatment regimen of minimally invasive therapy may be recommended.

Suitably said assay further comprises the step of
(h) determining if said sample stains abnormally with Wheat Germ Agglutinin lectin; wherein if (b) is abnormal and (c) is abnormal and low grade dysplasia is present, and
if (e) is abnormal then a treatment regimen of increased surveillance is selected. More suitably a treatment regimen of minimally invasive therapy may be recommended.

In all cases, if (b) is normal and/or (c) is normal and/or low grade dysplasia is absent, then a treatment regimen of normal surveillance is selected. Normal surveillance may vary depending on the subject; suitably normal surveillance means surveillance and the interval already ascribed for said subject.

In another aspect, the invention relates to a method of collecting information useful in determining prognosis for developing EAC, the method comprising
(a) providing an oesophagal sample from said subject
(b) determining if said sample stains abnormally with *Aspergillus oryzae* lectin;
(c) determining if there is a DNA content abnormality in said sample; and
(d) determining if there is low grade dysplasia in said sample.

In another aspect, the invention relates to an apparatus or system which is
(a) configured to analyse an oesophagal sample from a subject, wherein said analysis comprises
(b) determining if said sample stains abnormally with *Aspergillus oryzae* lectin;
(c) determining if there is a DNA content abnormality in said sample; and
(d) determining if there is low grade dysplasia in said sample;
said apparatus or system comprising an output module, wherein if (b) is abnormal and (c) is abnormal and low grade dysplasia is present, then said output module indicates an increased likelihood of progression to EAC for said subject.

Said apparatus or system may further be configured such that the analysis further comprises
(e) determining if said sample stains abnormally for CA19-9;
wherein if (b) is abnormal and (c) is abnormal and low grade dysplasia is present, and
if (e) is abnormal then said output module indicates a further increased likelihood of progression is determined.

Said apparatus or system may further be configured such that the analysis further comprises
(f) determining if said sample stains abnormally for Cyclin A;
wherein if (b) is abnormal and (c) is abnormal and low grade dysplasia is present, and
if (f) is abnormal then said output module indicates a further increased likelihood of progression is determined.

Said apparatus or system may further be configured such that the analysis further comprises
(g) determining if said sample stains abnormally for p53;
wherein if (b) is abnormal and (c) is abnormal and low grade dysplasia is present, and
if (g) is abnormal then said output module indicates a further increased likelihood of progression is determined.

Said apparatus or system may further be configured such that the analysis further comprises
(h) determining if said sample stains abnormally with Wheat Germ Agglutinin lectin; wherein if (b) is abnormal and (c) is abnormal and low grade dysplasia is present, and
if (h) is abnormal then said output module indicates a further increased likelihood of progression is determined.

The invention also relates to kits comprising AOL and/or WGA together with reagents for ICM DNA detection. The invention also relates to said kit(s) further comprising material capable of binding one or more of Cyclin A, p53, CA19-9.

Figure 1:
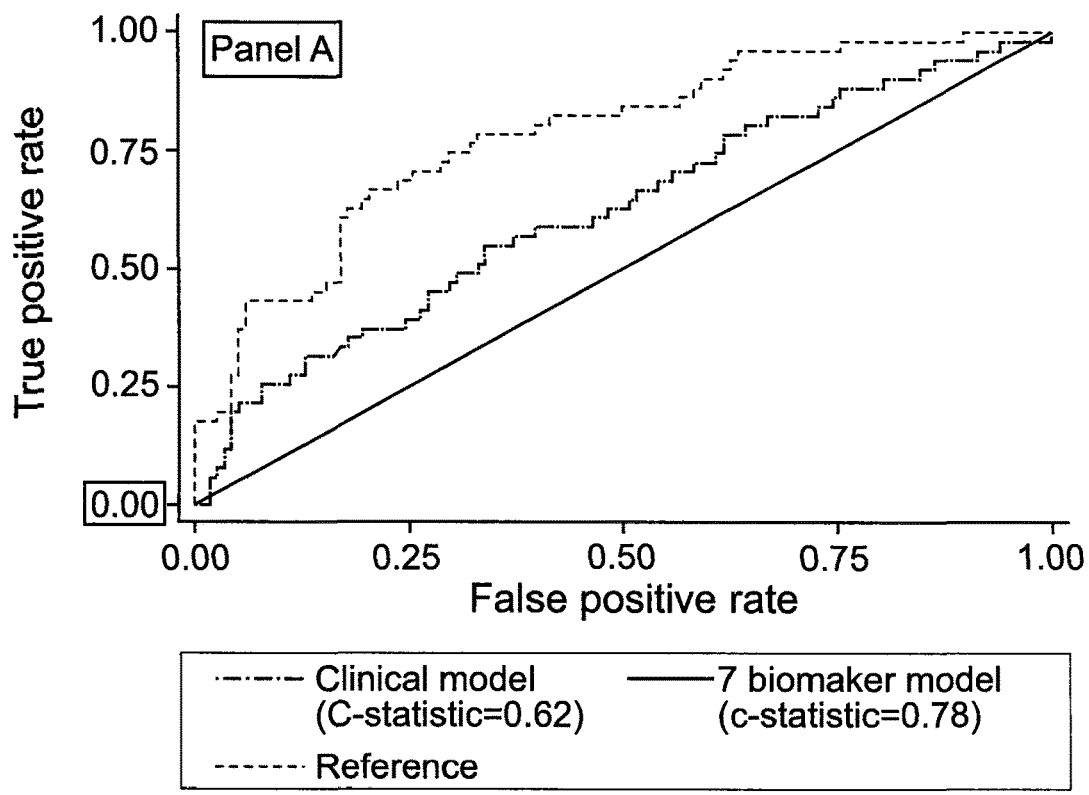
FIG. 1 shows ROC curve comparing 7 biomarker model (Panel A) and 3 biomarker model (Panel B) with basic clinical model (age, sex, presence of dysplasia, year of BE diagnosis).
Figure 1:
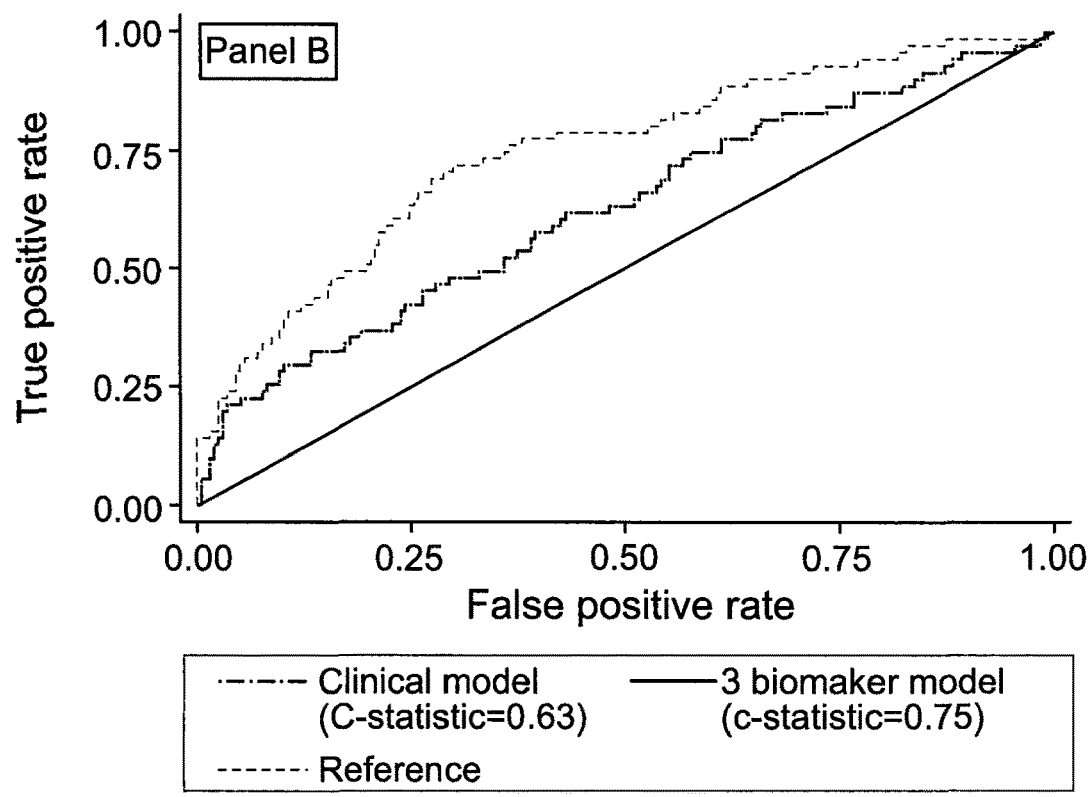

The invention is now described by way of example. These examples are intended to be illustrative, and are not intended to limit the appended claims.

EXAMPLES

Summary of the Examples

Methods: A nested case control study within the population-based Northern Ireland BE Register, (1993-2005). Cases (n=89) who progressed to EAC or HGD ≥6 months following diagnosis of BE were matched to non-progressor controls (n=291) for age/sex and year of BE diagnosis. Established (abnormal DNA content, p53 and cyclin A expression) and novel biomarkers (sialyl Lewis A and CD-15 expression, *Aspergillus oryzae* lectin (AOL) binding and Wheat germ agglutinin (WGA) lectin binding were assessed in paraffin embedded tissue from first BE diagnosis. Conditional logistic regression analysis was applied to investigate risk of progression.

Results: After a mean 6.7 (±3.2) years of follow-up, dysplasia and 7 biomarkers contributed to the risk of EAC/HGD in a multivariable analysis. Using a backward selection technique, a panel comprising low grade dysplasia and 2 biomarkers (abnormal DNA ploidy and AOL) was optimal for distinguishing progressors and non-progressors. When combined into a risk score for dysplastic (0-3) or non-dysplastic BE (0-2), the adjusted OR for progression was 3.74 (95% CI 2.43-5.79) and 2.99 (95% CI 1.72-5.20) for each point increase, respectively.

Conclusion: A panel of 3 biomarkers (sometimes discussed as 2 molecular biomarkers (DNA/AOL) plus dysplasia) can distinguish both dysplastic and non-dysplastic BE patients at higher risk for future development of EAC and HGD.

Example 1: Identification of Biomarker Panel

Using the population based Northern Ireland Barrett's Oesophagus Register (NIBR), we constructed a nested case-control study to investigate a panel of established and novel biomarkers on routinely collected paraffin embedded samples. One aim of this study was to determine whether dysplasia, DNA copy number, p53, cyclin A and the more recently described glycan targets (CA19-9, CD-15, WGA, AOL), were predictive of future progression to EAC from BE. Another aim was to create a biomarker panel which could be used as a quantitative risk stratification tool.

The methods arising from this study will be useful in a future phase 4 study.

Study Design

A nested case-control study was conducted within the Northern Ireland Barrett's Oesophagus Registry (NIBR), (20-22). The NIBR is a population-based register of all 9,329 adults diagnosed with columnar-lined oesophagus between 1993 and 2005 throughout Northern Ireland. Within the NIBR, 4,306 patients with a visible columnar lined segment displayed Specialized Intestinal Metaplasia (SIM) on biopsy and, for the purposes of this study, this definition was used for diagnosis of BE. Cases were BE patients from the NIBR who developed EAC, gastric cardia malignancies or HGD at least 6 months after their initial BE diagnosis. Cancer outcomes were identified by matching the NIBR to the Northern Ireland Cancer Registry database of oesophageal and gastric malignancies diagnosed up to 31 Dec. 2005. Gastric cardia cancers arising in BE patients were considered to be cases, as these are likely to be categorised as EAC cases under TNM7 HGD outcomes were identified as 2 separate clinical diagnoses within 12 months or 3 separate diagnoses of HGD regardless of time period. Each case was matched to up to 5 controls who were BE patients who had not developed EAC or HGD by the study censor date of 31 Dec. 2005, based on age (±5 years), sex and year of BE diagnosis. Ethical approval was granted by the regional ethics committee in Northern Ireland (REC No 07/NIR02/109).

Histopathology Review

All index and outcome biopsies were reviewed blindly by two independent expert gastrointestinal pathologists (MN & DM), and scored using the Vienna scale (23). Complete agreement was achieved in 84% of samples scored, with discrepancies resolved by discussion and a re-evaluation of the slide where necessary. Cases and controls were excluded if they did not have an index BE biopsy available for review taken ≥6 months prior to their HGD or cancer diagnosis. Any index BE samples that were scored by pathologists as having either no evidence of SIM or evidence of HGD and EAC (Vienna score of 4-5) at the outset of the study were excluded from the study. The histological diagnosis of the outcome biopsy was confirmed by both pathologists in 88% of EAC, 100% of gastric cardia and 83% of HGD outcome biopsies. Reasons for outcome biopsies not being histologically verified included no biopsy available or no HGD or EAC present in the tissue section cut from the outcome biopsy.

Image Cytometry DNA Analysis

One 40 μm section was cut from FFPE tissue and nuclear monolayers were prepared as previously described (24). The monolayer was then acid hydrolysed and stained with Feulgen-Schiff reagent using standardized methodology (13). All slides were given unique code identifiers and studied using an automated image cytometric analyser (Room 4, East Sussex, UK) that consists of a microscope (Axioplan 2, Zeiss, Jena, Germany), a 546-nm green filter, and a black-and-white, high-resolution digital camera (AxioCam MRm, Zeiss, Jena, Germany). Optical density and nuclear area were measured and integrated optical density of each nucleus was calculated as previously described (25). A histogram representing the DNA content was produced and analysed according to European Society for Analytical Cellular Pathology (ESACP) guidelines (26). DNA Ploidy-related parameters such as DNA index (DI) and percentages of cells exceeding 5c (5c ER) and 9c (9c ER) were also noted. All histograms were reported blindly by two of three independent observers (JD, DO and MN). Consensus was reached in all cases.

Immunohistochemistry

Immunohistochemistry was performed for p53 (1/50 dilution, retrieval H1 30 min, DO7, Leica, Milton Keynes), Cyclin A (1/50 dilution, retrieval H1 10 min, Leica), Sialyl Lewis a (BOND ready, retrieval H1 20 min, Leica) and CD15 (BOND ready, retrieval H2 20 min, Leica) on 4 μm section using the BOND autostainer (Leica, Milton Keynes, UK) following manufacturer instructions. Stained sections were then counterstained with a light haematoxylin stain.

Histochemistry

Slides were de-paraffinised according to standard procedures, placed in a humidified incubation chamber and 5 μg/mL of lectin (WGA or AOL) applied, followed by incubation at 37° C. for 15 minutes. WGA was obtained as Biotinylated wheat germ from Vector labs Catalog number V0428. AOL was prepared using AOL purchased from Tokyo Chemical Industry UK Ltd L0169, which was labelled with biotin using ProtOn labelling kit PLK-1202. The un-bound lectin was washed off by immersion in running water (2×30 mins), and mounted with Prolong Gold antifade reagent with DAPI (Invitrogen, Paisley, UK). The lectin-stained slides were scanned using Applied Imaging Ariol® (Genetex Ltd, Hampshire, UK).

p53 was stained with Leica Novocastra antibody clone D07.

CD15 was stained with Leica Novocastra antibody Carb-1 PA0039.

CA19-9 ($SL^a$ or $sLe^a$) was stained with Leica Novocastra antibody 241:5:1:4 PA0424.

Cyclin A was stained with Leica Novocastra antibody clone 6E6.

Scoring of Histo- and Immunohistochemistry p53 was scored as significant or non-significant. Strong, dark staining or total absent of staining next to normal background stain were significant. The percentage of cyclin A positive compared to negative epithelial surface cells was calculated. A cut off of 1% was used for significance.

Slides stained for CD15, $SL^a$, AOL and WGA were graded for intensity (0-3) and for the % of the area stained at this intensity (0-4). The H score (0-12), derived by multiplying intensity and area scores was calculated (0-12) (27) and provides more accurate scoring compared to either the intensity or area score alone. Four epithelial compartments were assessed: the apical epithelial membrane (apical part of the epithelial cell membrane which is exposed to the oesophageal lumen); pan membranous, epithelial mucous globule (globular collections of staining within the cytoplasm) and epithelial cytoplasm).

Statistical Analysis

Baseline characteristics between cases and controls were compared using independent t-tests for continuous variables and chi-squared tests for categorical variables. Conditional logistic regression was conducted to estimate odds ratios for neoplastic progression and corresponding 95% confidence intervals for each biomarker investigated. In analyses where a case failed to be assigned a biomarker score, both the case and its corresponding controls were excluded from that analysis. Multivariate analysis was adjusted for age, sex, year of BE diagnosis, and the presence of dysplasia (as scored by two expert pathologists).

The True Positive Rate (TPR) or sensitivity and False Positive Rate (FPR) or 1-specificity of biomarkers, were calculated by dividing the number of cases and controls, scored as abnormal by the total number of cases and controls scored for that biomarker. Positive Predictive Value (PPV) and Negative Predictive Value (NPV) for the entire cohort of individuals with BE were estimated from the nested case-control design, based upon the prevalence of cancer and HGD outcomes amongst the SIM positive patients at index Barrett's oesophagus diagnosis from the entire 1993-2005 population-based NIBR cohort (28).

Logistic regression was used to combine the seven biomarkers along with dysplasia, year of BE, age and sex into a risk score. Each biomarker score was dichotomised into abnormal or normal. For DNA copy number, p53 and cyclin A this was on the basis of a priori knowledge (for example for DNA copy number diploid normal, tetraploidy or aneuploidy abnormal). For CA 19-9, WGA, AOL and CD-15, each of the four components of the staining score were dichotomised into normal/abnormal based on the most frequent median distribution amongst controls and then summed to give an overall abnormal score of 0-4 for each biomarker.

To evaluate the performance of models, predicted probabilities were used to calculate the area under the receiver operating characteristic (ROC) curves (the c statistic) and to calculate the discrimination slope (the difference in mean predicted probability in the cases compared with the controls) (29). The performance of a clinical model (containing only dysplasia, year of BE, age and sex) was compared with the performance of a biomarker model containing all seven biomarkers (along with dysplasia year of BE, age and sex) using the c statistic and integrated discrimination improvement (IDI) (30). The IDI measures how much the biomarker model leads to increased estimated risks of cancer (or HGD) for cases and decreased estimated risks for controls, compared with the clinical model without biomarkers. Internal validation was conducted on the c statistics using bootstrap methods. Specifically, the model was estimated in a bootstrap sample and the c statistics was calculated in the bootstrap sample and in the original sample. This process was repeated 200 times and the average difference in performance in the bootstrap sample and in the original sample was calculated (the optimism) and subtracted from the apparent performance to estimate the internally validated performance (31).

A reduced model was selected using the stepwise backward selection procedure (using a cut off of 0.5), retaining age, year of BE and sex in the model. The internally validated c statistic for this model was calculated as described previously but after applying the stepwise selection procedure to each bootstrap sample. Validation of the model was conducted using logistic regression, rather than conditional logistic regression, for simplicity, but estimates from the logistic and conditional logistic models were similar (results not shown). Additional stratified analyses were repeated removing individuals without dysplasia at index biopsy.

Patient Demographics

After a mean (SD) follow-up period of 6.7 (3.3) years, 56 EAC, 13 gastric cardia cancers and 25 HGD cases were diagnosed within the study cohort. After review by two expert pathologists, five cases (2 EAC, 1 gastric cardia cancer and 2 HGD cases) were found to have evidence of HGD or EAC at their initial BE diagnosis and were therefore excluded from analysis, leaving 89 cases. Table 1 shows the characteristics of these 89 cases and their 291 matched controls. Cases and controls did not differ by matching criteria (age, sex and year of BE diagnosis), nor laboratory of origin or length of BE segment, although the latter was unknown for approximately half of participants. Significantly more cases were diagnosed as having indefinite or low grade dysplasia at their first BE diagnosis compared with controls, (20.2% versus 2.4% respectively), (p<0.001).

Conclusions

This population based phase 3 biomarker study has revealed a new combination panel for assessment of risk to progression from both dysplastic and non-dysplastic BE to EAC. The combination panel of 7 biomarkers represents a significant step to individualise patient risk and is advantageous due to the use of relatively simple techniques that can be carried out on formalin fixed tissue. Furthermore analysis of a simplified 3 biomarker panel model showed a significant stepwise increase risk of progression for AOL, DNA content abnormalities and presence of LGD.

This work was strengthened by the study design, using a well described cohort with long term follow up and in which all biomarker analysis was undertaken blinded to the outcome. The NIBR is a valuable population based resource, with over 4,000 adults diagnosed with visible columnar-lined oesophagus and SIM within Northern Ireland (population 1.8 million). The 89 cases of progression to HGD/EAC from BE represent a substantially larger number of endpoints than previous longitudinal studies of biomarkers in BE from other centres (32, 33). The majority of these patients were Caucasian middle aged males, which is concordant with previous epidemiological studies of BE. Importantly samples were collected as part of routine clinical care and hence are applicable to everyday practice. A weakness of this study is that limited biopsies were available for analysis and hence it was not possible to achieve data for all of the biomarkers in every patient.

Of the validated biomarkers, DNA content abnormalities measured by image cytometry were most predictive of HGD/cancer progression (OR=3.22; 95% CI 1.73-6.00; P<0.001). DNA ploidy abnormalities have been evaluated in prospective trials of patients with BE, representing phase 4 biomarker development (10, 11, 34). A landmark study by the Reid group demonstrated that patients who had both HGD and aneuploidy or tetraploidy had a five year cancer risk of 66%, compared to 42% with HGD alone and 28% with DNA ploidy abnormalities alone. Patients who had no cytometric abnormality (DNA diploid) and did not have HGD had a five year cancer risk of zero. [Reid et al., 2000b] The same group went on to evaluate the role of a chromosomal instability panel, combining 9pLOH, 17pLOH and DNA ploidy abnormalities. [30] The combination of all three was a better predictor of progression to EAC than any one biomarker alone (RR=38.7; 95% CI=10.8-138.5; p<0.001). These markers are not used in most centres however, as they require a combination of platforms that would be difficult to perform outside of specialist research centres. DNA content flow cytometry particularly is associated with inter laboratory variability, quality control issues and significant set up and running costs (35). The use of image cytometry rather than flow cytometry in this study therefore represents an advance as image cytometry is cheaper, easier to set up and has potential for automation. Although new single platform techniques to measure chromosomal instability, such as SNP and gene chip arrays (36), are being developed that may provide rapid throughput of FFPE material, the accuracy and cost implications for surveillance programmes remains unclear.

Of the novel biomarkers involved in glycan expression, CA19-9 and the lectin AOL were significant predictors of cancer development, although only AOL was included as a significant independent biomarker of neoplastic progression in the final reduced model. Both CA19-9 and AOL have previously been shown to be upregulated in the progression from metaplasia through dysplasia to cancer in Phase 2 studies (19, 37). AOL can be readily assessed following lectin histochemistry which is cheaper and simpler to perform than immunohistochemistry and ploidy techniques. However, AOL is also overexpressed in almost a quarter of BE controls who did not progress, thus limiting its specificity. Nevertheless, the intriguing possibility also exists that it may be possible to evaluate AOL positive areas endoscopically, as previously demonstrated for WGA lectin (19).

The strongest predictor of cancer progression was the presence of LGD by 2 expert GI pathologists (OR=11.33; 95% CI 3.97-32.36; p<0.01), although the overall presence in the cohort when assessed >5 years prior to progression was small (2.8%). In terms of the level of agreement between pathologists, 84% (21/25 patients) of LGD were scored by both specialist GI pathologists on first review, with consensus agreement of all 25 samples upon discussion/re-review. This is comparable with the Dutch consensus study (38) and more favourable than the study by Wani et al. (39).

The difficulty in grading LGD and the uncertainty of the risk of cancer in these patients (38, 39) has led to great debate about the advantages and disadvantages of treating LGD, particularly with the advent of minimally invasive endoscopic therapies (40, 41). The complexity of the issue is illustrated by the contrasting conclusions of two recent studies. In a Dutch study biopsies from 147 patients with LGD diagnosed by local hospital pathologists were reviewed by two expert GI pathologists. The initial diagnosis of LGD by the community pathologist was confirmed by one of the specialist GI pathologists in only 15% of patients (22/147), and the incidence rate of HGD or EAC in this consensus group was high at 13.4% (95% CI 3.5-23.2) per annum. In contrast, a study performed in the USA concluded that the risk of progression to HGD and EAC was no different from non-dysplastic BE even when consensus was reached. There are methodological differences which may affect these data, but overall it highlights the clinical challenges in the diagnosis of LGD. The possibility of utilising DNA ploidy and AOL analysis to more objectively determine the LGD patients at highest risk of progression requiring intensive surveillance or intervention is therefore appealing.

Abnormal cyclin A and p53 expression measured by IHC did not confer a significantly increased risk of HGD/EAC progression in multivariate analysis. The presence of TP53 did however show a significant risk in EAC alone (OR=1.95; 95% CI 1.04-3.67). A previous smaller case-control study from the NIBR of 29 patients who progressed to EAC and 6 patients who progressed to HGD, had shown that TPS3 expression was associated with a higher increased risk of progression (OR=11.7, 95% CI, 1.93-71.4). [41] In a more recent case control study of 54 BE patients, 27 of whom progressed to HGD/EAC and 27 non-progressors, moderate p53 overexpression was also associated with a significantly increased risk of progression with a HR of 6.5 (95% CI, 2.5-17.1) (42). The interpretation of these results is limited by inter laboratory variability of TP53 IHC (43). The gold standard for measurement of p53 mutations is gene sequencing, which is more specific than TP53 IHC, although this is not routinely available and would be technically difficult given the small size and heterogeneity inherent to endoscopic biopsy. p53 expression measured by IHC is a relatively simple technique that is widely available in pathology laboratories, and in our phase 3 study we were able to demonstrate a small but significant risk to cancer progression but this was lost when combined with HGD. The utility of p53, when compared to the other biomarkers in our panel, is therefore likely to be limited. Cyclin A negativity, which has been previously been postulated as a marker of low risk of progression was of borderline significance which dropped out on multivariate analysis. It was interesting that the association with cyclin A was stronger in the 'EAC only' outcomes though, suggesting it may be more useful at identifying patients in the later stages of progression from HGD to cancer.

We have demonstrated that the combination of multiple biomarkers confer a higher risk of progression than any one biomarker alone. Using the combination panel, 67% of cases had 2-4 abnormal markers on the index biopsies. In other words, although the presence of a positive biomarker panel confers a greater risk of progression to HGD/EAC in this study, a third of patients without these abnormalities could still progress. This may be explained by sampling error, both from biopsy at endoscopy and when cutting additional sections from archival FFPE tissue blocks. There may also be a temporal effect if the biopsies at baseline were taken too early before the onset of cancer. When we evaluated the risk of progression in HGD/EAC diagnosed within or after the median time to progression of 3.6 years, there was a trend for AOL to be a better marker of later progression than DNA copy number or LGD. Importantly, on adjusted analysis none of the tests for interaction between markers and follow-up time were significant, as the numbers involved were too small for meaningful analysis. Caution must therefore be exercised in the interpretation of a negative biomarker panel and a reduction of the frequency of endoscopic surveillance on the basis of our panel could not be recommended until these markers are investigated in future Phase 4/5 studies.

With the introduction of minimally invasive endoscopic therapy for the ablation of BE, there is an increasing need to risk stratify patients accurately, as treatment may be offered at an earlier stage. The biomarker panel described here therefore has practical clinical implications and further provides a useful algorithm for risk stratification— i. No dysplasia and panel negative Risk unknown. Continue current surveillance interval.

ii. No dysplasia and panel positive

Moderate-High risk according to panel. Increase surveillance and consider minimally invasive therapy if >2 positive.

iii. Consensus LGD/IND+any one biomarker positive

High risk. Consider minimally invasive therapy.

The combination of dysplasia scoring, DNA ploidy status and AOL may provide significant economic savings as the LGD group, which currently equates to an annual surveillance interval according to AGA guidelines, may be more accurately stratified by biomarkers into a moderate risk group with standard surveillance and higher risk group for ablation. This strategy would benefit from being evaluated in a phase V biomarker study before uptake into routine clinical practice.

In conclusion this study has demonstrated that a 7 biomarker panel is a clinically applicable and useful tool for risk stratification in BE. Our results further demonstrate that a reduced panel of 3 biomarkers is advantageous over a clinical model using pathological dysplasia diagnosis, age and sex alone in identifying BE patients at risk of developing HGD/EAC. Our results are consistent with previous longitudinal studies of single biomarkers, including TP53 abnormalities and DNA content abnormalities. That our panel can be undertaken on paraffin embedded tissue and was undertaken on clinical rather than research samples increase its wider application. This panel could be applied to biopsies of BE at diagnosis, has the potential to guide surveillance and therapeutic intervention with expected public health and financial benefit.

Example 2

Figure 2:
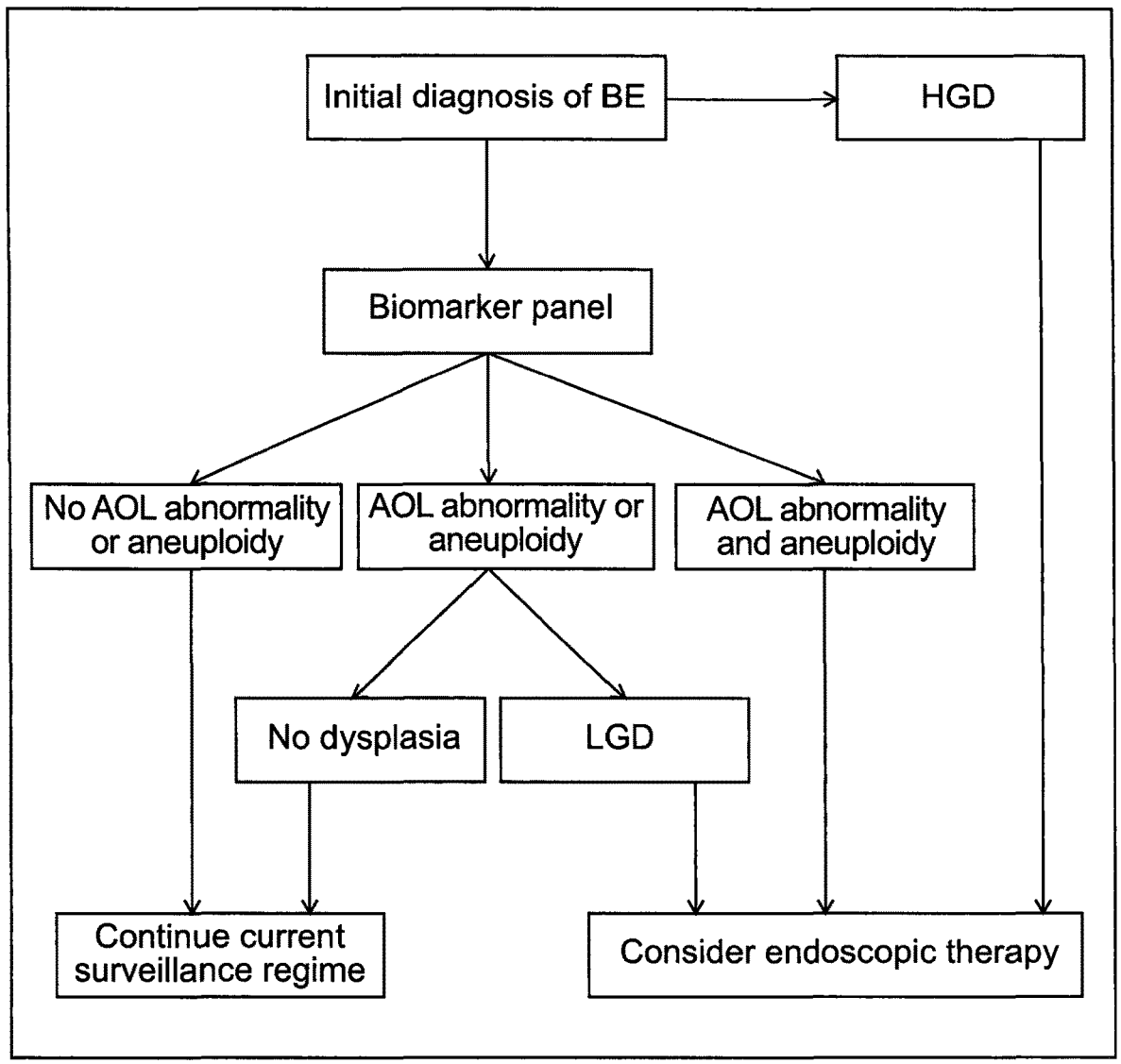
FIG. 2 shows the clinical algorithm for application of the biomarker panel of the invention to clinical practice. LGD=low grade dysplasia; HGD=high grade dysplasia; AOL=*Aspergillus oryzae* lectin.

FIG. 2 presents a method (algorithm) of the invention.

In one embodiment the finding of (no dysplasia, but AOL OR aneuploidy positive) could lead to recommendation to have slightly more frequent surveillance e.g. annual rather than 2-3 yearly. However it must be noted that surveillance intervals are being lengthened in general in most current guidelines to 3-5 years for low risk.

TABLE 1

Characteristics of cases and matched controls

| Characteristic | Cases n = 89 (%) | Controls n = 291 (%) | p-value |
|---|---|---|---|
| Gender | | | |
| Male | 67 (75.3) | 218 (74.9) | 0.94 |
| Female | 22 (24.7) | 73 (25.1) | |
| Age at BE diagnosis | | | |
| (mean ± SD, years) | 63.8 ± 11.9 | 63.8 ± 11.3 | 0.99 |
| Length BE segment | | | |
| Long | 43 (48.3) | 141 (48.45) | 0.59 |
| Short | 1 (1.1) | 9 (3.1) | |
| Unknown | 45 (50.6) | 141 (48.45) | |
| Laboratory of origin | | | |
| Altnagelvin | 21 (23.6) | 46 (15.8) | 0.27 |
| Antrim | 19 (21.3) | 79 (27.1) | |
| Belfast City | 11 (12.3) | 52 (17.9) | |
| Craigavon | 7 (7.9) | 16 (5.5) | |
| Royal Victoria | 31 (34.8) | 98 (33.7) | |
| Vienna score of index BE* | | | |
| 1 | 71 (79.8) | 284 (97.6) | <0.001 |
| 2-3 | 18 (20.2) | 7 (2.4) | |

*Vienna score 1: intestinal metaplasia; 2-3: indefinite or low grade dysplasia, as scored by two expert gastrointestinal pathologists.

TABLE 2

Adjusted risk of progressing from BE according to markers in the initial oesophageal biopsies

| Marker | Cases N | Controls n | TPR (95% CI) | FPR (95% CI) | Estimated PPV | Estimated NPV | Cancer + HGD Adjusted OR (95% CI) | Cancer only Adjusted OR (95% CI) |
|---|---|---|---|---|---|---|---|---|
| 'Standard' Dysplasia | | | | | | | | |
| None | 56 | 262 | 0.31 (0.21-0.42) | 0.08 (0.05-0.12) | 0.08 | 0.98 | 1.00 | 1.00 |
| Indefinite/LGD | 25 | 22 | | | | | 22.69 (6.47-79.53) | 24.86 (5.57-111.04) |
| Unknown | 8 | 7 | | | | | 7.30 (2.06-25.81) | 6.03 (1.47-24.79) |
| p for trend | | | | | | | 0.001 | 0.007 |
| 'Expert' Dysplasia | | | | | | | | |
| None | 71 | 284 | 0.20 (0.13-0.30) | 0.02 (0.01-0.05) | 0.15 | 0.98 | 1.00 | 1.00 |
| Indefinite/LGD | 18 | 7 | | | | | 11.78 (4.31-32.18) | 13.22 (3.67-47.59) |
| p for trend | | | | | | | <0.001 | <0.001 |
| DNA copy number | | | | | | | | |
| Diploid | 44 | 201 | 0.44 (0.33-0.55) | 0.15 (0.11-0.21) | 0.06 | 0.99 | 1.00 | 1.00 |
| Abnormal[a] | 34 | 35 | | | | | 3.22 (1.73-6.00) | 3.03 (1.57-5.83) |
| p for trend | | | | | | | <0.001 | 0.001 |
| Cyclin A | | | | | | | | |
| Negative/Low % positive[b] | 59 | 205 | 0.25 (0.16-0.37) | 0.16 (0.12-0.21) | 0.03 | 0.98 | 1.00 | 1.00 |
| Positive | 20 | 39 | | | | | 1.32 (0.66-2.66) | 1.73 (0.81-3.69) |
| p for trend | | | | | | | 0.43 | 0.16 |
| p53 | | | | | | | | |
| 0 (None) | 18 | 83 | | | | | 1.00 | 1.00 |
| 1 (Focal) | 25 | 103 | | | | | 1.02 (0.48-2.16) | 0.87 (0.39-1.91) |
| 2 (Diffuse) | 20 | 62 | | | | | 1.21 (0.50-2.94) | |
| 3 (intense) | 15 | 30 | | | | | 1.39 (0.63-3.09) | 3.61 (1.39-9.37) |
| p for trend | | | | | | | | 0.02 |

TABLE 2-continued

Adjusted risk of progressing from BE according to markers in the initial oesophageal biopsies

| Marker | Cases N | Controls n | TPR (95% CI) | FPR (95% CI) | Estimated PPV | Estimated NPV | Cancer + HGD Adjusted OR (95% CI) | Cancer only Adjusted OR (95% CI) |
|---|---|---|---|---|---|---|---|---|
| 2-3 v. 0-1 | | | 0.45 (0.34-0.57) | 0.33 (0.28-0.39) | 0.03 | 0.98 | 2.12 (0.87-5.16) 0.08 1.60 (0.91-2.82) | 1.95 (1.04-3.67) |
| CA19-9 Lectin[c] | | | | | | | | |
| 0-1 scores | 33 | 151 | | | | | 1.00 | 1.00 |
| abnormal | 34 | 91 | | | | | 1.44 (0.81-2.58) | 1.38 (0.75-2.54) |
| 2-3 scores abnormal | 18 | 29 | | | | | 3.32 (1.48-7.43) | 2.49 (0.98-6.31) 0.05 |
| 4 scores abnormal[d] | | | 0.61 (0.50-0.71) | 0.44 (0.38-0.50) | 0.03 | 0.99 | 0.004 1.77 (1.04-3.00) | 1.56 (0.88-2.76) |
| p for trend |||||||||
| 2-4 v. 0-1 |||||||||
| WGA[c] | | | | | | | | |
| 0-1 scores | 15 | 63 | | | | | 1.00 | 1.00 |
| abnormal | 61 | 189 | | | | | 1.43 (0.68-3.01) | 1.54 (0.70-3.36) |
| 2-3 scores abnormal | 2 | 1 | | | | | 9.33 (0.69-126.21) | / 0.36 |
| 4 scores abnormal[e] | | | 0.81 (0.70-0.88) | 0.75 (0.69-0.80) | 0.02 | 0.99 | 0.11 1.46 (0.69-3.06) | 1.53 (0.70-3.34) |
| p for trend |||||||||
| 2-4 v. 0-1 |||||||||
| CD-15[c] | | | | | | | | |
| 0-1 scores | 63 | 186 | | | | | 1.00 | 1.00 |
| abnormal | 14 | 63 | | | | | 0.50 (0.24-1.03) | 0.52 (0.24-1.16) |
| 2-3 scores abnormal | 9 | 15 | | | | | 1.84 (0.69-4.90) | 1.37 (0.48-3.92) 0.92 |
| 4 scores abnormal[e] | | | 0.27 (0.18-0.38) | 0.30 (0.24-0.36) | 0.02 | 0.98 | 0.77 0.74 (0.41-1.33) | 0.70 (0.36-1.36) |
| p for trend |||||||||
| 2-4 v. 0-1 |||||||||
| AOL[c] | | | | | | | | |
| 0-1 scores | 42 | 177 | | | | | 1.00 | 1.00 |
| abnormal | 39 | 61 | | | | | 3.17 (1.74-5.77) | 3.38 (1.74-6.55) |
| 2-3 scores abnormal | 0 | 2 | | | | | / | / 0.001 |
| 4 scores abnormal[e] | | | 0.48 (0.37-0.59) | 0.26 (0.21-0.32) | 0.04 | 0.99 | 0.002 3.10 (1.71-5.63) | 3.38 (1.74-6.55) |
| p for trend |||||||||
| 2-4 v. 0-1 |||||||||

Legend for Table 2:

TPR: True Positive Rate, equivalent to sensitivity. FPR: False Positive Rate, equivalent to 1-specificity.

PPV: Positive Predictive Value. NPV: Negative Predictive Value. TPR, FPR, PPV and NPV refer to analysis of cancer and HGD cases.

Adjustments: age, gender, year BE diagnosis. All other biomarkers were further adjusted for dysplasia.

[a]Abnormal includes aneuploid, tetraploid, aneuploid & tetraploid and hypodiploid

[b]Low % positive defined as <1% positive.

[c]CA19-9, WGA, CD-15 and AOL all had four components of tissue staining assessed: apical membrane, pan membranous, epithelial mucous globules and epithelial cytoplasm.

[d]Biomarker scores considered abnormal if highest score for apical membrane, epithelial mucous globules or epithelial cytoplasm was 0-<4, or pan membranous was 0.

[e]Biomarker scores considered abnormal if highest score for apical membrane, epithelial mucous globules or epithelial cytoplasm was 4-12, or pan membranous was >0.

TABLE 3

Adjusted risk of progressing from BE according to markers in the initial oesophageal biopsies

| Variable | Full sample (51 cases, 118 controls) | | | Individuals without dysplasia at initial biopsy (39 cases, 87 controls) | | | Cancer outcomes only (36 cases, 85 controls) | | |
| --- | --- | --- | --- | --- | --- | --- | --- | --- | --- |
| | Cases (%) | Controls (%) | Full model* adjusted OR (95% CI) | Cases (%) | Controls (%) | Full model* adjusted OR (95% CI) | Cases (%) | Controls (%) | Full model* adjusted OR (95% CI) |
| Dysplasia | 10 (20%) | 5 (4%) | 2.57 (0.62, 10.72) | | | | 8 (22%) | 3 (4%) | 6.28 (1.08, 36.49) |
| DNA copy number abnormal | 25 (49%) | 18 (15%) | 4.93 (2.09, 11.61) | 15 (38%) | 13 (15%) | 4.46 (1.69, 11.71) | 16 (44%) | 14 (16%) | 3.91 (1.35, 11.31) |
| Cyclin A abnormal | 12 (24%) | 24 (20%) | 1.29 (0.48, 3.47) | 7 (18%) | 22 (25%) | 0.81 (0.28, 2.37) | 8 (22%) | 17 (20%) | 1.00 (0.30, 3.45) |
| P53 abnormal | 21 (41%) | 33 (28%) | 1.61 (0.72, 3.60) | 14 (36%) | 24 (28%) | 1.84 (0.74, 4.58) | 15 (42%) | 17 (20%) | 3.54 (1.28, 9.81) |
| CA199 abnormal | 30 (59%) | 58 (49%) | 1.28 (0.54, 3.01) | 21 (54%) | 42 (48%) | 1.15 (0.44, 2.95) | 19 (53%) | 45 (53%) | 0.61 (0.22, 1.71) |
| WGA abnormal | 41 (80%) | 91 (77%) | 0.95 (0.37, 2.47) | 29 (74%) | 66 (76%) | 0.75 (0.27, 2.07) | 29 (81%) | 66 (78%) | 0.99 (0.30, 3.30) |
| CD15 abnormal | 13 (25%) | 38 (32%) | 0.95 (0.36, 2.49) | 11 (29%) | 25 (29%) | 1.04 (0.37, 2.94) | 9 (25%) | 27 (32%) | 0.63 (0.19, 2.12) |
| AOL abnormal | 25 (49%) | 24 (20%) | 3.78 (1.69, 8.37) | 15 (38%) | 17 (20%) | 2.97 (1.20, 7.35) | 16 (44%) | 13 (15%) | 4.84 (1.67, 14.04) |
| Model performance c statistic | | | | | | | | | |
| Basic model† | | | 0.62 (0.53, 0.72) | | | 0.52 (0.41, 0.63) | | | 0.66 (0.54, 0.77) |
| Basic model plus all biomarkers shown | | | 0.78 (0.71, 0.86) | | | 0.73 (0.64, 0.82) | | | 0.80 (0.72, 0.88) |
| Internally validated c statistic§ | | | | | | | | | |
| Basic model† | | | 0.56 (0.47, 0.66) | | | 0.43 (0.32, 0.54) | | | 0.59 (0.47, 0.70) |
| Basic model plus all biomarkers shown | | | 0.71 (0.64, 0.79) | | | 0.63 (0.53, 0.74) | | | 0.70 (0.62, 0.78) |
| Discrimination slope | | | | | | | | | |
| Basic model† | | | 0.07 | | | 0.00 | | | 0.09 |
| Basic model plus all biomarkers shown | | | 0.22 | | | 0.13 | | | 0.25 |
| IDI | | | 0.15 | | | 0.13 | | | 0.16 |

*Full model contains age at diagnosis, sex, year of BE and all biomarkers shown.
†Basic model contains dysplasia (except in subgroup excluding dysplasia), age at diagnosis, sex and year of BE.
§See methods for more details.

TABLE 4

Adjusted risk of progressing from BE according to markers in the initial oesophageal biopsies model based upon backward selection.

| Variable | Full sample (71 cases, 197 controls) | | | Individuals without dysplasia at initial biopsy (54 cases, 149 controls) | | | Cancer outcomes only (52 cases, 146 controls) | | |
|---|---|---|---|---|---|---|---|---|---|
| | Cases (%) | Controls (%) | Reduced model* adjusted OR (95% CI) | Cases (%) | Controls (%) | Reduced model* adjusted OR (95% CI) | Cases (%) | Controls (%) | Reduced model* adjusted OR (95% CI) |
| Dysplasia | 14 (20%) | 6 (3%) | 4.30 (1.36, 13.65) | | | | 10 (19%) | 4 (3%) | 5.63 (1.43, 22.18) |
| DNA copy number abnormal | 32 (45%) | 28 (14%) | 3.05 (1.61, 5.82) | 19 (34%) | 23 (15%) | 3.25 (1.55, 6.81) | 20 (38%) | 23 (16%) | 2.73 (1.24, 6.03) |
| AOL abnormal | 32 (45%) | 44 (22%) | 4.27 (2.16, 8.43) | 22 (39%) | 32 (21%) | 2.78 (1.38, 5.59) | 22 (42%) | 27 (18%) | 3.13 (1.46, 6.72 |
| Model performance c statistic | | | | | | | | | |
| Basic model† | | | 0.63 (0.54, 0.70) | | | 0.51 (0.42, 0.60) | | | 0.64 (0.55, 0.73) |
| Basic model plus AOL and IC DNA | | | 0.75 (0.68, 0.81) | | | 0.68 (0.59, 0.77) | | | 0.72 (0.64, 0.81) |
| Internally validated c statistic§ | | | | | | | | | |
| Basic model† | | | 0.57 (0.48, 0.64) | | | 0.42 (0.33, 0.51) | | | 0.57 (0.48, 0.66) |
| Basic model plus AOL and IC DNA | | | 0.69 (0.62, 0.75) | | | 0.57 (0.48, 0.66) | | | 0.68 (0.60, 0.77) |
| Discrimination slope | | | | | | | | | |
| Basic model† | | | 0.08 | | | 0.00 | | | 0.09 |
| Basic model plus AOL and IC DNA | | | 0.18 | | | 0.12 | | | 0.15 |
| IDI | | | 0.10 | | | 0.12 | | | 0.06 |

*Reduced model contains age at diagnosis, sex, year of BE, AOL and IC DNA.
†Basic model contains (except in subgroup excluding dysplasia), age at diagnosis, sex and year of BE.
§See methods for more details.

TABLE 5

Risk scores of BE individuals scored as abnormal for dysplasia, DNA copy number and AOL.

| Risk score count | Cases | Controls | Cut off | True positive rate | False positive rate |
|---|---|---|---|---|---|
| All BE | | | | | |
| 0 | 19 | 126 | ≥0 versus <0 | 100% | 100% |
| 1 | 35 | 64 | ≥1 versus <1 | 73% | 36% |
| 2 | 8 | 7 | ≥2 versus <2 | 24% | 4% |
| 3 | 9 | 0 | ≥3 versus <3 | 13% | 0% |
| OR per point increase *= 3.74 (2.43, 5.79), P < 0.001 | | | | | |
| Non-dysplastic BE | | | | | |
| 0 | 19 | 98 | >0 versus <0 | 100% | 100% |
| 1 | 33 | 47 | >1 versus <1 | 66% | 34% |
| 2 | 4 | 4 | >2 versus <2 | 7% | 3% |
| OR per point increase *= 2.99 (1.72, 5.20), P < 0.001 | | | | | |

*Adjusted for age, sex and year of BE.

REFERENCES

1. Vial M, Grande L, Pera M. Epidemiology of adenocarcinoma of the esophagus, gastric cardia, and upper gastric third. *Recent Results Cancer Res.* 2010; 182:1-17.

2. Kadri S R, Lao-Sirieix P, O'Donovan M, et al. Acceptability and accuracy of a non-endoscopic screening test for Barrett's oesophagus in primary care: cohort study. *Bmj.* 2010; 341:c4372.

3. Group MRCOCW. Surgical resection with or without preoperative chemotherapy in oesophageal cancer: a randomised controlled trial. *Lancet.* 2002 May 18; 359 (9319):1727-33.

4. Sikkema M, de Jonge P J, Steyerberg E W, et al. Risk of esophageal adenocarcinoma and mortality in patients with Barrett's esophagus: a systematic review and meta-analysis. *Clin Gastroenterol Hepatol.* 2010 March; 8(3):235-44; quiz e32.

5. Desai T K, Krishnan K, Samala N, et al. The incidence of oesophageal adenocarcinoma in non-dysplastic Barrett's oesophagus: a meta-analysis. *Gut.* 2011 Oct. 13.

6. Yousef F, Cardwell C, Cantwell M M, et al. The incidence of esophageal cancer and high-grade dysplasia in Barrett's esophagus: a systematic review and meta-analysis. *Am J Epidemiol.* 2008 Aug. 1; 168(3):237-49.

7. Reid B J, Li X, Galipeau P C, et al. Barrett's oesophagus and oesophageal adenocarcinoma: time for a new synthesis. *Nat Rev Cancer.* 2010 February; 10(2):87-101.

8. Sullivan Pepe M, Etzioni R, Feng Z, et al. Phases of biomarker development for early detection of cancer. *J Natl Cancer Inst.* 2001 Jul. 18; 93(14):1054-61.

9. Lao-Sirieix P, Lovat L, Fitzgerald R C. Cyclin A immunocytology as a risk stratificataion tool for Barrett's esophagus surveillance. *Clin Cancer Res.* 2007; 13(2): 659-65.
10. Reid B J, Levine D S, Longton G, et al. Predictors of progression to cancer in Barrett's esophagus: baseline histology and flow cytometry identify low- and high-risk patient subsets. *Am J Gastroenterol.* 2000 July; 95(7): 1669-76.
11. Rabinovitch P S, Longton G, Blount P L, et al. Predictors of progression in Barrett's esophagus III: baseline flow cytometric variables. *Am J Gastroenterol.* 2001 November; 96(11):3071-83.
12. Dunn J M, Mackenzie G D, Oukrif D, et al. Image cytometry accurately detects DNA ploidy abnormalities and predicts late relapse to high-grade dysplasia and adenocarcinoma in Barrett's oesophagus following photodynamic therapy. *Br J Cancer.* 2010 May 25; 102(11): 1608-17.
13. Chao D L, Sanchez C A, Galipeau P C, et al. Cell Proliferation, Cell Cycle Abnormalities, and Cancer Outcome in Patients with Barrett's Esophagus: A Long-term Prospective Study. *Clinical Cancer Research.* 2008 Nov. 1, 2008; 14(21):6988-95.
14. Casson A G, Tammemagi M, Eskandarian S, et al. p53 alterations in oesophageal cancer: association with clinicopathological features, risk factors, and survival. *Mol Pathol.* 1998 April; 51(2):71-9.
15. Ribeiro U, Finkelstein S D, Safatle-Ribeiro A V, et al. p53 sequence analysis predicts treatment response and outcome of patients with esophageal carcinoma. *Cancer.* 1998:83(1):7-18.
16. Kuroki T, Fujiwara Y, Nakamori S, et al. Evidence for the presence of two tumour-suppressor genes for hepatocellular carcinoma on chromosome 13q. *Br J Cancer.* 1995 August; 72(2):383-5.
17. Jorgensen T, Berner A, Kaalhus O, et al. Up-regulation of the oligosaccharide sialyl LewisX: a new prognostic parameter in metastatic prostate cancer. *Cancer Res.* 1995 May 1; 55(9):1817-9.
18. Futamura N, Nakamura S, Tatematsu M, et al. Clinicopathologic significance of sialyl Le(x) expression in advanced gastric carcinoma. *Br J Cancer.* 2000 December; 83(12):1681-7.
19. Bird-Lieberman E L, Neves A A, Lao-Sirieix P, et al. Molecular imaging using fluorescent lectins permits rapid endoscopic identification of dysplasia in Barrett's esophagus. *Nature Med.* 2011; In Press.
20. Murray L, Watson P, Johnston B, et al. Risk of adenocarcinoma in Barrett's oesophagus: population based study. *Bmj.* 2003 Sep. 6;327(7414):534-5.
21. Coleman H, Bhat S, Murray L et al. Increasing incidence of Barrett's oesophagus: a population-based study. *European Journal of Epidemiology.* 2011; 26(9):739-45.
22. Bhat S, Coleman H G, Yousef F, et al. Risk of malignant progression in Barrett's esophagus patients: results from a large population-based study. *J Natl Cancer Inst.* 2011 Jul. 6; 103(13):1049-57.
23. Schlemper R J, Riddell R H, Kato Y, et al. The Vienna classification of gastrointestinal epithelial neoplasia. *Gut.* 2000 Aug. 1, 2000:47(2):251-5.
24. Pretorius M E, Waehre H, Abeler V M, et al. Large scale genomic instability as an additive prognostic marker in early prostate cancer. *Cell Oncol.* 2009:31(4):251-9.
25. Bondi J, Pretorius M, Bukholm L et al. Large-scale genomic instability in colon adenocarcinomas and correlation with patient outcome. *Apmis.* 2009 October; 117 (10):730-6.
26. Haroske G, Book J P, Danielsen H, et al. Fourth updated ESACP consensus report on diagnostic DNA image cytometry. *Anal Cell Pathol.* 2001; 23(2):89-95.
27. Cronin J, McAdam E, Danikas A, et al. Epidermal growth factor receptor (EGFR) is overexpressed in high-grade dysplasia and adenocarcinoma of the esophagus and may represent a biomarker of histological progression in Barrett's esophagus (BE). *Am J Gastroenterol.* 2011 January; 106(1):46-56.
28. Baker S G, Kramer B S, Srivastava S. Markers for early detection of cancer: statistical guidelines for nested case-control studies. *BMC Med Res Methodol.* 2002; 2:4.
29. Steyerberg E W. Clinical prediction models: A practical approach to development, validation and updating: Springer; 2008.
30. Pencina M J, D'Agostino R B, Sr., D'Agostino R B, Jr., et al. Evaluating the added predictive ability of a new marker: from area under the ROC curve to reclassification and beyond. *Stat Med.* 2008 Jan. 30:27(2):157-72; discussion 207-12.
31. Steyerberg E W, Harrell F E, Jr., Borsboom G J, et al. Internal validation of predictive models: efficiency of some procedures for logistic regression analysis. *J Clin Epidemiol.* 2001 August; 54(8):774-81.
32. Galipeau P C, Li X, Blount P L, et al. NSAIDs modulate CDKN2A, TP53, and DNA content risk for progression to esophageal adenocarcinoma. *PLoS Med.* 2007 February; 4(2):e67.
33. Schulmann K, Sterian A, Berki A, et al. Inactivation of p16, RUNX3, and HPP1 occurs early in Barrett's-associated neoplastic progression and predicts progression risk. *Oncogene.* 2005 Jun. 9; 24(25):4138-48.
34. Reid B J, Prevo L J, Galipeau P C, et al. Predictors of progression in Barrett's esophagus II: baseline 17p (p53) loss of heterozygosity identifies a patient subset at increased risk for neoplastic progression. *Am J Gastroenterol.* 2001 October; 96(10):2839-48.
35. Reid B J, Blount P L, Rubin C E. et al. Flow-cytometric and histological progression to malignancy in Barrett's esophagus: prospective endoscopic surveillance of a cohort. *Gastroenterology.* 1992 April; 102(4 Pt 1):1212-9.
36. Paulson T G, Maley C C, Li X, et al. Chromosomal instability and copy number alterations in Barrett's esophagus and esophageal adenocarcinoma. *Clin Cancer Res.* 2009 May 15:15(10):3305-14.
37. Bird-Lieberman E L, Dunn J M, P. L-S, et al. Phase 2 and phase 3 multicentre studies demonstrate the potential for glycans as predictive biomarkers in Barrett's oesophagus *Gut.* 2011; 60(Suppl 1):A169-70.
38. Hvid-Jensen F, Pedersen L, Drewes A M, et al. Incidence of Adenocarcinoma among Patients with Barrett's Esophagus. *N Engl J Med.* 2011 Oct. 13:365(15):1375-83.
39. Wani S, Falk G W, Post J, et al. Risk Factors for Progression of Low-Grade Dysplasia in Patients With Barrett's Esophagus. *Gastroenterology.* 2011 October; 141 (4):1179-86 el.
40. Bulsiewicz W J, Shaheen N J. The role of radiofrequency ablation in the management of Barrett's esophagus. *Gastrointest Endosc Clin N Am.* 2011 January; 21 (1):95-109.
41. Spechler S J, Sharma P, Souza R F, et al. American Gastroenterological Association medical position statement on the management of Barrett's esophagus. *Gastroenterology.* 2011 March; 140(3):1084-91.
42. Sikkema M, de Jonge P J, Steyerberg E W, et al. Risk of Esophageal Adenocarcinoma and Mortality in Patients With Barrett's Esophagus: A Systematic Review and Meta-Analysis. *Clin Gastroenterol Hepatol.* 2009 Oct. 19.
43. Alsner J, Jensen V, Kyndi M, et al. A comparison between p53 accumulation determined by immunohistochemistry and TP53 mutations as prognostic variables in tumours from breast cancer patients. *Acta Oncol.* 2008; 47(4):600-7.

All publications mentioned in the above specification are herein incorporated by reference. Various modifications and variations of the described aspects and embodiments of the present invention will be apparent to those skilled in the art without departing from the scope of the present invention.

Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

---

The invention claimed is:

1. A method for determining likelihood of progression from Barrett's esophagus to high grade dysplasia or esophageal adenocarcinoma in a human subject with Barrett's esophagus using an assay device, which includes a biomarker panel, the method comprising:
   (a) providing an oesophagal sample from said human subject, and using the sample for detection of fragments of biomarkers in the sample;
   (b) staining said sample with biotinylated *Aspergillus oryzae* lectin (AOL) and determining whether the stained sample produces an abnormal stain based on determination of a staining score, the staining requires an assay that stains, the biotinylated *Aspergillus oryzae* lectin is *Aspergillus oryzae* lectin, which is labelled with biotin; and
   (c) determining if a DNA copy number in said sample is abnormal using image cytometry DNA analysis, the DNA copy number diploid being normal, and the DNA copy number tetraploidy or aneuploidy being abnormal; and
   (d) determining if there is low grade dysplasia in said sample,
   wherein, in a first determination, if (b) is abnormal and (c) is abnormal and low grade dysplasia is present, then the likelihood of said progression is determined to be higher for said human subject compared to the likelihood of said progression for an equivalent subject, in a second determination, demonstrating all of the following: a normal stain in step (b); a normal DNA copy in step (c) and no low grade dysplasia, wherein:

step (d) includes histological examination of the sample, and scoring one of the presence and absence of low grade dysplasia using a Vienna scale, the assay device includes the biomarker panel including a material, which binds to and has affinity for AOL, and the determining whether the stained sample produces an abnormal stain based on determination of the staining score includes:

staining a plurality of components, the plurality of components includes apical membrane, pan membranous, epithelial mucous globules and epithelial cytoplasm;

determining a level of staining by the AOL, for each component, by:
(a) grading the intensity of the stain and the percentage of the area stained at said intensity, and
(b) producing, based on the level of the staining for each component, an H score; and comparing for each component, of the plurality of components, to determine if the H score is abnormal, the comparing including:
the H score considered abnormal if highest score for apical membrane, epithelial mucous globules or epithelial cytoplasm was 4-12, or pan membranous was >0;

based on the comparing, dichotomizing each of the components of the staining score into one of normal and abnormal;

summing, the results of the dichotomizing, to provide an overall abnormal score for the components; and comparing the overall abnormal score to a reference to determine if the stained sample is abnormal.

2. A method according to claim 1, further comprising step (e) determining if staining for CA 19-9 produces an abnormal stain,
wherein if (b) is abnormal and (c) is abnormal and low grade dysplasia is present, and if (e) is abnormal then the likelihood of progression to esophageal adenocarcinoma is determined to be greater than if (e) is normal.

3. An assay, which includes a biomarker panel, for selecting a treatment regimen for a human subject with Barrett's esophagus, said assay comprising
(a) providing an oesophagal sample from said human subject, and using the sample for detection of fragments of biomarkers in the sample;
(b) staining said sample with biotinylated *Aspergillus oryzae* lectin (AOL) and determining whether the stained sample produces an abnormal stain based on determination of a staining score, wherein the staining requires an assay that stains, the biotinylated *Aspergillus oryzae* lectin is *Aspergillus oryzae* lectin, which is labelled with biotin;
(c) determining if a DNA copy number in said sample is abnormal using image cytometry DNA analysis, the DNA copy number diploid being normal, and the DNA copy number tetraploidy or aneuploidy being abnormal; and
(d) determining if there is low grade dysplasia in said sample, wherein:
if (b) is abnormal and (c) is abnormal and low grade dysplasia is present, then a treatment regimen including-surveillance is selected,
step (d) includes histological examination of the sample, and scoring one of the presence and absence of low grade dysplasia using a Vienna scale,
the assay device includes the biomarker panel including a material, which binds to and has affinity for AOL, and the determining whether the stained sample produces an abnormal stain based on determination of the staining score includes:

staining a plurality of components, the plurality of components includes apical membrane, pan membranous, epithelial mucous globules and epithelial cytoplasm;

determining a level of staining by the AOL, for each component, by:
(a) grading the intensity of the stain and the percentage of the area stained at said intensity, and
(b) producing, based on the level of the staining for each component, an H score; and comparing for each component, of the plurality of components, to determine if the H score is abnormal, the comparing including:
the H score considered abnormal if highest score for apical membrane, epithelial mucous globules or epithelial cytoplasm was 4-12, or pan membranous was >0;

based on the comparing, dichotomizing each of the components of the staining score into one of normal and abnormal;

summing, the results of the dichotomizing, to provide an overall abnormal score of for the components; and comparing the overall abnormal score to a reference to determine if the stained sample is abnormal.

4. A method according to claim 1, wherein said sample comprises formalin fixed paraffin embedded material.

5. A method according to claim 1 wherein step (c) comprises determining the DNA copy number by image cytometry DNA analysis and inferring from said determination whether said DNA copy number is abnormal.

6. A method for treating a human subject with Barrett's esophagus, which includes a biomarker panel, the method comprising:
(a) providing an oesophagal sample from said human subject, and using the sample for detection of fragments of biomarkers in the sample;
(b) determining if staining said sample with biotinylated *Aspergillus oryzae* lectin (AOL) produces an abnormal stain based on determination of a staining score, wherein the staining requires an assay that stains, the biotinylated *Aspergillus oryzae* lectin is *Aspergillus oryzae* lectin, which is labelled with biotin,
(c) determining if a DNA copy number in said sample is abnormal using image cytometry DNA analysis, the DNA copy number diploid being normal, and the DNA copy number tetraploidy and aneuploidy being abnormal; and
(d) determining if there is low grade dysplasia in said sample, wherein:
if (b) is abnormal and (c) is abnormal and low grade dysplasia is present, then treating said subject with increased surveillance for progression from Barrett's esophagus to high grade dysplasia or esophageal adenocarcinoma,
step (d) includes histological examination of the sample, and scoring one of the presence and absence of low grade dysplasia using a Vienna scale,
the assay device includes the biomarker panel including a material, which binds to and has affinity for AOL, and
the determining if staining said sample with biotinylated *Aspergillus oryzae* lectin (AOL) produces an abnormal stain based on determination of a staining score includes:

staining a plurality of components, the plurality of components includes apical membrane, pan membranous, epithelial mucous globules and epithelial cytoplasm;

determining a level of staining by the AOL, for each component, by:
   (a) grading the intensity of the stain and the percentage of the area stained at said intensity, and
   (b) producing, based on the level of the staining for each component, an H score; and comparing for each component, of the plurality of components, to determine if the H score is abnormal, the comparing including:
   the H score considered abnormal if highest score for apical membrane, epithelial mucous globules or epithelial cytoplasm was 4-12, or pan membranous was >0;

based on the comparing, dichotomizing each of the components of the staining score into one of normal and abnormal;

summing, the results of the dichotomizing, to provide an overall abnormal score for the components; and comparing the overall abnormal score to a reference to determine if the stained sample is abnormal.

7. The method according to claim 1, wherein the oesophagal sample is provided on a glass slide.

8. The method according to claim 3, wherein the oesophagal sample is provided on a glass slide.

9. The method according to claim 6, wherein the oesophagal sample is provided on a glass slide.

10. The method according to claim 1, wherein the biomarker panel includes a polypeptide marker.

* * * * *

SEQUENCE LISTING

<160> NUMBER OF SEQ ID NOS: 4

<210> SEQ ID NO 1
<211> LENGTH: 310
<212> TYPE: PRT
<213> ORGANISM: Aspergillus oryzae

<400> SEQUENCE: 1

```
Met Ser Thr Pro Gly Ala Gln Glu Val Leu Phe Arg Thr Gly Ile Ala
1               5                   10                  15

Ala Val Asn Ser Thr Asn His Leu Arg Val Tyr Phe Gln Asp Ser His
                20                  25                  30

Gly Ser Ile Arg Glu Ser Leu Tyr Glu Ser Gly Trp Ala Asn Gly Thr
            35                  40                  45

Ala Lys Asn Val Ile Ala Lys Ala Lys Leu Gly Thr Pro Leu Ala Ala
        50                  55                  60

Thr Ser Lys Glu Leu Lys Asn Ile Arg Val Tyr Ser Leu Thr Glu Asp
65                  70                  75                  80

Asn Val Leu Gln Glu Ala Ala Tyr Asp Ser Gly Ser Gly Trp Tyr Asn
                85                  90                  95

Gly Ala Leu Ala Gly Ala Lys Phe Thr Val Ala Pro Tyr Ser Arg Ile
                100                 105                 110

Gly Ser Val Phe Leu Ala Gly Thr Asn Ala Leu Gln Leu Arg Ile Tyr
            115                 120                 125

Ala Gln Lys Thr Asp Asn Thr Ile Gln Glu Tyr Met Trp Asn Gly Asp
        130                 135                 140

Gly Trp Lys Glu Gly Thr Asn Leu Gly Val Ala Leu Pro Gly Thr Gly
145                 150                 155                 160

Ile Gly Val Thr Cys Trp Arg Tyr Thr Asp Tyr Asp Gly Pro Ser Ile
                165                 170                 175

Arg Val Trp Phe Gln Thr Asp Asn Leu Lys Leu Val Gln Arg Ala Tyr
                180                 185                 190

Asp Pro His Thr Gly Trp Phe Lys Glu Leu Thr Thr Ile Phe Asp Lys
            195                 200                 205

Ala Pro Pro Arg Cys Ala Ile Ala Ala Thr Asn Phe Asn Pro Gly Lys
        210                 215                 220

Ser Ser Ile Tyr Met Arg Ile Tyr Phe Val Asn Ser Asp Asn Thr Ile
225                 230                 235                 240

Trp Gln Val Cys Trp Asp His Gly Gln Gly Tyr His Asp Lys Arg Thr
                245                 250                 255

Ile Thr Pro Val Ile Gln Gly Ser Glu Ile Ala Ile Ile Ser Trp Glu
            260                 265                 270

Gly Pro Glu Leu Arg Leu Tyr Phe Gln Asn Gly Thr Tyr Val Ser Ala
        275                 280                 285

Ile Ser Glu Trp Ser Trp Ala Arg His Gly Ser Gln Leu Gly Arg Arg
    290                 295                 300

Ala Leu Pro Pro Ala Glu
```

305                 310

<210> SEQ ID NO 2
<211> LENGTH: 431
<212> TYPE: PRT
<213> ORGANISM: Homo sapiens

<400> SEQUENCE: 2

Met Leu Gly Asn Ser Ala Pro Gly Pro Ala Thr Arg Glu Ala Leu Gly
1               5                   10                  15

Ala Ala Ser Ile Ala Ala Asp Gly Ala Pro Arg Gly Pro Gly Glu Tyr
            20                  25                  30

Gln Pro Gly Lys Gly Ser Ala Arg Pro Thr Thr Ala Asp Pro Gly Ala
        35                  40                  45

Leu Ala Val Leu Lys Ser Gly Asn Pro Arg Gly Leu Ala His Glu Gln
    50                  55                  60

Arg Pro Lys Thr Arg Arg Val Ala Pro Leu Lys Asp Leu Pro Val Asn
65                  70                  75                  80

Asp Glu His Val Thr Val Pro Pro Trp Lys Ala Asn Ser Lys Gln Pro
                85                  90                  95

Ala Phe Thr Ile His Val Asp Glu Ala Glu Lys Glu Ala Gln Lys Lys
            100                 105                 110

Pro Ala Glu Ser Gln Lys Ile Glu Arg Glu Asp Ala Leu Ala Phe Asn
        115                 120                 125

Ser Ala Ile Ser Leu Pro Gly Pro Arg Lys Pro Leu Val Pro Leu Asp
    130                 135                 140

Tyr Pro Met Asp Gly Ser Phe Glu Ser Pro His Thr Met Asp Met Ser
145                 150                 155                 160

Ile Val Leu Glu Asp Glu Lys Pro Val Ser Val Asn Glu Val Pro Asp
                165                 170                 175

Tyr His Glu Asp Ile His Thr Tyr Leu Arg Glu Met Glu Val Lys Cys
            180                 185                 190

Lys Pro Lys Val Gly Tyr Met Lys Lys Gln Pro Asp Ile Thr Asn Ser
        195                 200                 205

Met Arg Ala Ile Leu Val Asp Trp Leu Val Glu Val Gly Glu Glu Tyr
    210                 215                 220

Lys Leu Gln Asn Glu Thr Leu His Leu Ala Val Asn Tyr Ile Asp Arg
225                 230                 235                 240

Phe Leu Ser Ser Met Ser Val Leu Arg Gly Lys Leu Gln Leu Val Gly
                245                 250                 255

Thr Ala Ala Met Leu Leu Ala Ser Lys Phe Glu Glu Ile Tyr Pro Pro
            260                 265                 270

Glu Val Ala Glu Phe Val Tyr Ile Thr Asp Asp Thr Tyr Thr Lys Lys
        275                 280                 285

Gln Val Leu Arg Met Glu His Leu Val Leu Lys Val Leu Thr Phe Asp
    290                 295                 300

Leu Ala Ala Pro Thr Val Asn Gln Phe Leu Thr Gln Tyr Phe Leu His
305                 310                 315                 320

Gln Gln Pro Ala Asn Cys Lys Val Glu Ser Leu Ala Met Phe Leu Gly
                325                 330                 335

Glu Leu Ser Leu Ile Asp Ala Asp Pro Tyr Leu Lys Tyr Leu Pro Ser
            340                 345                 350

Val Ile Ala Gly Ala Ala Phe His Leu Ala Leu Tyr Thr Val Thr Gly
        355                 360                 365

```
Gln Ser Trp Pro Glu Ser Leu Ile Arg Lys Thr Gly Tyr Thr Leu Glu
    370                 375                 380

Ser Leu Lys Pro Cys Leu Met Asp Leu His Gln Thr Tyr Leu Lys Ala
385                 390                 395                 400

Pro Gln His Ala Gln Gln Ser Ile Arg Glu Lys Tyr Lys Asn Ser Lys
                405                 410                 415

Tyr His Gly Val Ser Leu Leu Asn Pro Pro Glu Thr Leu Asn Leu
                420                 425                 430

<210> SEQ ID NO 3
<211> LENGTH: 393
<212> TYPE: PRT
<213> ORGANISM: Homo sapiens

<400> SEQUENCE: 3

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Cys
                165                 170                 175

Pro His His Glu Arg Cys Ser Asp Ser Asp Gly Leu Ala Pro Pro Gln
                180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Lys Glu Asn
275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320
```

```
Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
            370                 375                 380

Phe Lys Thr Glu Gly Pro Asp Ser Asp
385             390

<210> SEQ ID NO 4
<211> LENGTH: 186
<212> TYPE: PRT
<213> ORGANISM: Triticum turgidum

<400> SEQUENCE: 4

Gln Arg Cys Gly Glu Gln Gly Ser Gly Met Glu Cys Pro Asn Asn Leu
1               5                   10                  15

Cys Cys Ser Gln Tyr Gly Tyr Cys Gly Met Gly Gly Asp Tyr Cys Gly
            20                  25                  30

Lys Gly Cys Gln Asn Gly Ala Cys Trp Thr Ser Lys Arg Cys Gly Ser
            35                  40                  45

Gln Ala Gly Gly Lys Thr Cys Pro Asn Asn His Cys Cys Ser Gln Tyr
        50                  55                  60

Gly His Cys Gly Phe Gly Ala Glu Tyr Cys Gly Ala Gly Cys Gln Gly
65              70                  75                  80

Gly Pro Cys Arg Ala Asp Ile Lys Cys Gly Ser Gln Ala Gly Gly Lys
            85                  90                  95

Leu Cys Pro Asn Asn Leu Cys Cys Ser Gln Trp Gly Tyr Cys Gly Leu
            100                 105                 110

Gly Ser Glu Phe Cys Gly Glu Gly Cys Gln Asn Gly Ala Cys Ser Thr
            115                 120                 125

Asp Lys Pro Cys Gly Lys Asp Ala Gly Gly Arg Val Cys Thr Asn Asn
            130                 135                 140

Tyr Cys Cys Ser Lys Trp Gly Ser Cys Gly Ile Gly Pro Gly Tyr Cys
145                 150                 155                 160

Gly Ala Gly Cys Gln Ser Gly Gly Cys Asp Gly Val Phe Ala Glu Ala
                165                 170                 175

Ile Ala Thr Asn Ser Thr Leu Leu Ala Glu
            180                 185
```